(12) United States Patent
Steele et al.

(10) Patent No.: US 7,308,367 B2
(45) Date of Patent: Dec. 11, 2007

(54) WAFER INSPECTION SYSTEM

(75) Inventors: M. Brandon Steele, Decatur, GA (US); Jeffrey Alan Hawthorne, Decatur, GA (US); Chunho Kim, Duluth, GA (US); David C. Sowell, Atlanta, GA (US)

(73) Assignee: Qcept Technologies, Inc., Atlanta, GA (US)

( * ) Notice: Subject to any disclaimer, the term of this patent is extended or adjusted under 35 U.S.C. 154(b) by 157 days.

(21) Appl. No.: 10/771,628

(22) Filed: Feb. 3, 2004

(65) Prior Publication Data

US 2004/0241890 A1   Dec. 2, 2004

Related U.S. Application Data

(63) Continuation-in-part of application No. 10/631,469, filed on Jul. 29, 2003.

(60) Provisional application No. 60/444,504, filed on Feb. 3, 2003.

(51) Int. Cl.
*G01B 5/28* (2006.01)

(52) U.S. Cl. .......................... 702/35; 702/36
(58) Field of Classification Search ................ 702/35, 702/36; 324/765; 438/12, 200, 906; 134/1.2, 134/1.3
See application file for complete search history.

(56) References Cited

U.S. PATENT DOCUMENTS

| | | | |
|---|---|---|---|
| 4,166,974 A | 9/1979 | Vermeers | |
| 4,295,092 A | 10/1981 | Okamura | |
| 4,481,616 A | 11/1984 | Matey | |
| 4,973,910 A | 11/1990 | Wilson | |
| 5,087,533 A | 2/1992 | Brown | |
| 5,136,247 A | 8/1992 | Hansen | |
| 5,214,389 A | 5/1993 | Cao et al. | |
| 5,217,907 A | 6/1993 | Bulucea et al. | |
| 5,218,362 A | 6/1993 | Mayes et al. | |
| 5,270,664 A | 12/1993 | McMurtry et al. | |
| 5,272,443 A | 12/1993 | Winchip et al. | |

(Continued)

FOREIGN PATENT DOCUMENTS

DE          297509 A5         1/1992

(Continued)

OTHER PUBLICATIONS

Reid, Jr., Lennox Errol, "Surface Characterization of Hard Disks Using Non-Contact Work Function Capacitance Probe," A Thesis Presented to the Academic Faculty in Partial Fulfillment of the Requirements for the Degree of Master of Science in Mechanical Engineering, Georgia Institute of Technology, Jun. 1986.

(Continued)

*Primary Examiner*—John Barlow
*Assistant Examiner*—Stephen J. Cherry
(74) *Attorney, Agent, or Firm*—Foley & Lardner LLP

(57) ABSTRACT

A method and system for identifying a defect or contamination on a surface of a material. The method and system involves providing a material, such as a semiconductor wafer, using a non-vibrating contact potential difference sensor to scan the wafer, generate contact potential difference data and processing that data to identify a pattern characteristic of the defect or contamination.

44 Claims, 23 Drawing Sheets

U.S. PATENT DOCUMENTS

| | | | |
|---|---|---|---|
| 5,278,407 | A | 1/1994 | Ikebe et al. |
| 5,293,131 | A | 3/1994 | Semones et al. |
| 5,315,259 | A | 5/1994 | Jostlein |
| 5,369,370 | A | 11/1994 | Stratmann et al. |
| 5,381,101 | A | 1/1995 | Bloom et al. |
| 5,460,684 | A | 10/1995 | Saeki et al. |
| 5,517,123 | A | 5/1996 | Zhao et al. |
| 5,546,477 | A * | 8/1996 | Knowles et al. ............ 382/242 |
| 5,583,443 | A | 12/1996 | McMurtry et al. |
| 5,723,980 | A | 3/1998 | Haase et al. |
| 5,723,981 | A | 3/1998 | Hellemans et al. |
| 5,773,989 | A | 6/1998 | Edelman et al. |
| 5,974,869 | A | 11/1999 | Danyluk et al. |
| 5,977,788 | A | 11/1999 | Lagowski |
| 6,011,404 | A * | 1/2000 | Ma et al. ................... 324/765 |
| 6,037,797 | A | 3/2000 | Lagowski et al. |
| 6,091,248 | A | 7/2000 | Hellemans et al. |
| 6,094,971 | A | 8/2000 | Edwards et al. |
| 6,097,196 | A | 8/2000 | Verukuil et al. |
| 6,114,865 | A | 9/2000 | Lagowski et al. |
| 6,127,289 | A | 10/2000 | Debusk |
| 6,139,759 | A | 10/2000 | Doezema et al. |
| 6,198,300 | B1 | 3/2001 | Doezema et al. |
| 6,201,401 | B1 | 3/2001 | Hellemans et al. |
| 6,232,134 | B1 | 5/2001 | Farber et al. |
| 6,255,128 | B1 | 7/2001 | Chacon et al. |
| 6,265,890 | B1 | 7/2001 | Chacon et al. |
| 6,517,669 | B2 | 2/2003 | Chapman |
| 6,520,839 | B1 | 2/2003 | Gonzalez-Martin et al. |
| 6,538,462 | B1 | 3/2003 | Lagowski et al. |
| 6,546,814 | B1 | 4/2003 | Choe et al. |
| 6,551,972 | B1 | 4/2003 | Lei et al. |
| 6,597,193 | B2 | 7/2003 | Lagowski et al. |
| 6,664,546 | B1 | 12/2003 | McCord et al. |
| 6,664,800 | B2 | 12/2003 | Chacon et al. |
| 6,680,621 | B2 | 1/2004 | Savtchouk et al. |
| 6,717,413 | B1 | 4/2004 | Danyluk et al. |
| 2002/0140564 | A1 | 10/2002 | Danyluk et al. |
| 2002/0186036 | A1 | 12/2002 | Smith |
| 2003/0052374 | A1 | 3/2003 | Lee et al. |
| 2003/0129776 | A1 | 7/2003 | Eom et al. |
| 2003/0139838 | A1 | 7/2003 | Marella |
| 2003/0164942 | A1 | 9/2003 | Take |
| 2003/0175945 | A1 | 9/2003 | Thompson et al. |
| 2004/0029131 | A1 | 2/2004 | Thompson et al. |
| 2004/0057497 | A1 | 3/2004 | Lagowski et al. |
| 2004/0058620 | A1 | 3/2004 | Gotkis et al. |
| 2004/0105093 | A1 | 6/2004 | Hamamatsu et al. |
| 2004/0134515 | A1 | 7/2004 | Castrucci |

FOREIGN PATENT DOCUMENTS

| | | |
|---|---|---|
| EP | 1039227 | 9/2000 |
| EP | 1304463 | 4/2003 |
| WO | WO 01/90730 A2 | 11/2001 |

OTHER PUBLICATIONS

Moorman, M. et al., "A Novel, Micro-Contact Potential Difference Probe," Sensors and Actuators B, Elsevier Sequoia S.A., Lausanne, CH, vol. 94, No. 1.

B Scruton and B.H. Blott, A High Resolution Probe for Scanning Electrostatic Potential Profiles Across Surfaces; Journal of Physics E: Scientific Instruments (May 1973), pp. 472-474; vol. 6, No. 5, Printed in Great Britain.

Yano D et al: "Nonvibrating contact potential difference probe measurement of a nanometer-scale lubricant on a hard disk", Journal of Tribology, American Society of Mechanical Engineers, New York, NY, US; vol. 121, No. 4, Oct. 1999, pp. 980-983, XP008031092, ISSN: 0742-4787 (pp. 980-981, fig. 4, first ref. on p. 983).

Castaldini A et al: "Surface analyses of polycrystalline and Cz-Si wafers", Solar Energy Materials and Solar Cells, Elsevier Science Publishers, Amsterdam, NL; vol. 72, No. 1-4, Apr. 2002, pp. 425-432, XP004339790, ISSN: 0927-0248 (whole document).

Korach C S et al: "Measurement of perfluoropolyether lubricant thickness on a magnetic disk surface", Applied Physics Letters, American Institute of Physics, New York, NY, US; vol. 79, No. 5, Jul. 30, 2001, pp. 698-700, XP012029958, ISSN: 0003-6951 (p. 699, left column; fig.2).

Yang Y et al: "Kelvin probe study on the perfluoropolyether film on metals", Tribology Letters, 2001, Kluwer Academic/Plenum Publishers, USA, vol. 10, No. 4, pp. 211-216, XP009035197, ISSN: 1023-8883 (p. 211-p. 212).

Castaldini A et al: "Scanning Kelvin probe and surface photovoltage analysis of multicrystalline silicon", Materials Science and Engineering B., Elsevier Sequoia, Lausanne, CH; vol. 91-92, Apr. 30, 2002, pp. 234-238, XP004355534, ISSN: 0921-5107 (chapters "2.2 Scanning Kelvin probe: and 4.2 Scanning Kelvin probe analyses").

Lagel B et al: "A novel detection system for defects and chemical contamination in semiconductors based upon the scanning Kelvin probe", 14th International Vacuum Congress (IVC-14). 10th International Conference on Solid Surfaces (ICS-10). 5th International Conference on Nanometre-Scale Science and Technology (NANO-5). 10th International Conference on Quantitative Surface Analysis; vol. 433-435, pp. 622-626, XP002292441, Surface Science, Aug. 2, 1999, Elsevier, NL, ISSN: 003906028 (whole document).

Ren J et al: "Scanning Kelvin Microscope: a new method for surface investigations" 8. Arbeitstatgung Angewandte Oberflachenanalytik 'AOFA 8' ('Applied Surface Analysis'), Kaiserslautern, DE, Sep. 5-8, 1994; vol. 353, No. 3-4, pp. 303-306, XP009035181, Fresenius' Journal of Analytical Chemistry, Oct. 1995, Springer-Verlag, DE, ISSN: 0937-0633 (p. 304, right column; fig. 1).

Baumgartner H et al: "Micro Kelvin probe for local work-function measurements", Review of Scientific Instruments, May 1988, USA; vol. 59, No. 5, pp. 802-805, XP0022922442, ISSN: 0034-6748 (abstract; fig. 4, chapter "V. Results").

Danyluk S: "Non-vibrating contact potential imaging for semiconductor fabrication", Semicon West 2003, 'Online!, Jul. 14, 2003, pp. 1-15, XP002292443, retrieved from the internet: ,URL:http://dom.semi.org/web/wFiles.nsf/Lookup/TIS18_QceptTechnologiesInc/$file/TIS18%20QceptTechnologiesInc.Alternate.pdf. retrieved on Aug. 13, 2004 (whole document).

* cited by examiner

WAFER INSPECTION SYSTEM

CROSS-REFERENCE TO RELATED PATENT APPLICATIONS

This application is related to as a continuation-in-part and claims priority from copending U.S. patent application Ser. No. 10/631,469 file Jul. 29, 2003 which claims priority from U.S. Prov. Pat. App. Ser. No. 60/444,504 filed Feb. 3, 2003.

FIELD OF THE INVENTION

The present invention is directed to methods and systems for the inspection of semiconductor wafers and other materials such as integrated circuits (IC) and any surface benefiting from inspection. Hereinafter, any material susceptible of surface inspection by the system herein described contact potential difference imaging device will be denoted a "wafer". More particularly, the present invention is directed to a method and system for the characterization of microscopic and macroscopic defects through imaging and visualization of the contact potential difference topology on the wafer surface through the use of a non-vibrating contact potential difference sensor.

BACKGROUND OF THE INVENTION

The multi-billion dollar global market for semiconductor defect management is growing both in absolute terms and as a percentage of semiconductor capital equipment investment. In general, there are two factors that determine the economics of a semiconductor fabrication facility at a given utilization level, namely throughput and yield. As complex new technologies such as 300 mm wafers, copper interconnects, and reduced feature (circuit) sizes drive the margin of error in fabrication ever lower, new inspection technologies are critical to keep yields high and bottom-line economics attractive. Detection and elimination of chemical contamination and other types of defects is a constant concern for semiconductor manufacturers and equipment suppliers. Contamination can arise from use of processing chemicals, processing equipment, and poor handling techniques. Contaminants can include, for example, metals, carbon, and organic compounds. Other types of defects can result from a wide range of causes, including flaws in the semiconductor crystal, improper processing, improper handling, and defective materials. In addition, many cleaning steps are required in wafer fabrication, such as but not limited to the semiconductor industry. Each step is time consuming and requires expensive chemicals that may require special disposal procedures. Existing methods for monitoring or controlling these processes are expensive and time consuming. As a result, wafers are often cleaned for a longer period of time and using more chemicals than are required.

Defect detection and characterization systems can be divided into in-line and off-line systems. "In-line" refers to inspection and measurement that takes place inside the clean room where wafers are processed. "Off-line" refers to analysis that takes place outside of the wafer processing clean room, often in a laboratory or separate clean room that is located some distance from the manufacturing area. In addition, many of these analytical techniques are destructive, which requires either the sacrifice of a production wafer or the use of expensive "monitor" wafers for analysis. In-line inspection and measurement is crucial for rapidly identifying and correcting problems that may occur periodically in the manufacturing process. A typical semiconductor wafer can undergo over 500 individual process steps and require weeks to complete. Each semiconductor wafer can have a finished product value of up to $100,000. Because the number of steps and period of time, involved in wafer fabrication are so large, a lot of work in process can exist at any point in time. It is critical that process-related defects be found and corrected immediately before a large number (and dollar value) of wafers are affected. Such defects, regardless of the nature of the wafer, semiconductor, IC, or other device, are detrimental to performance and diminish productivity and profitability.

Many types of defects and contamination are not detectable using existing in-line tools, and these are typically detected and analyzed using expensive and time-consuming "off line" techniques (described below) such as Total Reflectance X-ray Fluorescence (TXRF), Vapor Phase Decomposition Inductively Coupled Plasma-Mass Spectrometry (VPD ICP-MS) or Secondary Ion Mass Spectrometry (SIMS). Since these techniques are used off-line (outside of the clean room used to process wafers) and usually occur hours, or even days, after the process step that has caused the contamination, their value is significantly limited.

A brief description of some well known techniques for wafer inspection and chemical contamination detection are presented in Table 1. This list is not in any sense exhaustive as there are a very large number of techniques that are used for some type of semiconductor analysis or characterization or for other surface inspection of other types of materials.

TABLE 1

| Analytical Technique | Description | In-line/Off-line |
| --- | --- | --- |
| Total Reflection X-Ray Fluorescence (TXRF) | X-rays irradiate the wafer within the critical angle for total external reflectance, causing surface atoms to fluoresce. | Off-line |
| Automated Optical Microscopy | Optical images are acquired and automatically analyzed for detection of large defects. | In-line |
| Laser Backscattering | Wafer surface is illuminated with laser spots and the angle and/or polarization of reflected light is analyzed to detect and classify particles. | In-line |
| Vapor Phase Decomposition Inductively Coupled-Mass Spectrometry (VPD ICP-MS) | Wafers "scanned" with a drop of HF that is analyzed using mass spectrometry. | Off-line |
| Secondary Ion Mass Spectroscopy (SIMS) | Ion beam sputters the wafer surface creating secondary ions that are analyzed in a mass spectrometer. | Off-line |

Table 2 summarizes some major advantages and disadvantages of each example technique. In general, off-line detection techniques are extremely sensitive to tiny amounts of contamination; but are slow, expensive, and complex to operate. Some have limited, or no, imaging or surface mapping capability, or are destructive in nature. In-line techniques are much faster, non-destructive, and provide defect mapping, but have limited chemical contamination detection or analysis capability.

TABLE 2

| Analytical Technique | Advantages | Disadvantages |
|---|---|---|
| Total Reflection X-Ray Fluorescence (TXRF) | Very sensitive<br>Some mapping capability<br>Nondestructive | Limited coverage<br>Unpatterned wafers only |
| Automated Optical Microscopy | Fast<br>Relatively low cost<br>Detects a wide range of macro defects (>50 microns)<br>Imaging of wafer surface<br>Non-contact/non-destructive | Very limited chemical and particle detection |
| Laser Backscattering | Fast<br>Relatively low cost<br>Detects very small particles<br>Imaging of water surface<br>Non-contact/non-destructive | Only detects particles - no chemistry |
| Vapor Phase Decomposition Inductively Coupled-Mass Spectrometry (VPD ICP-MS) | Very sensitive<br>Able to identify wide range of contaminants | Destructive<br>Slow<br>Expensive<br>Complex<br>Cannot image<br>Only works on bare silicon |
| Secondary Ion Mass Spectroscopy (SIMS) | Very sensitive<br>Detects a wide range of contaminants<br>Sub-surface detection | Expensive<br>Slow<br>Destructive |

In general, existing in-line wafer inspection tools operate at production speeds and generate images of the wafer surface that are processed to identify and locate defects. However, these techniques are, as mentioned above, very limited in their ability to detect chemical contamination. Laser backscattering systems are limited to detecting particles down to sub-micron sizes, and optical microscopy systems can only detect chemical contamination that results in a visible stain or residue. Both techniques lack the ability to identify or classify the chemical composition of the particle or contamination. Off-line laboratory techniques are used to qualify the cleanliness of new processes and equipment, or to analyze defects detected by in-line equipment or as part of failure analysis.

Another system that has been investigated is the use of Contact Potential Difference imaging (CPD). CPD refers to the electrical contact between two different metals and the electrical field that develops as a result of the differences in their respective maximum electronic energy level, i.e. their respective Fermi energies. When two metals are placed in contact, the Fermi energies of each will equilibrate by the flow of electrons from the metal with the lower Fermi energy to that of the higher. "Vibrating CPD sensor" refers to the vibration of one metal relative to the other in a parallel plate capacitor system. The vibration induces changes in the capacitance with time, and therefore a signal related with the surface profile. A CPD signal can also be generated by the translation of one surface past a reference sample through the use of a non-vibrating contact potential difference (nvCPD) sensor(s). This translation makes high speed scanning possible.

However, even these nvCPD sensors can themselves present certain difficulties. At a microscopic level, the surfaces of wafers are not flat due to wafer thickness variation, materials on the surface, "bowing", and other factors. In order to scan the wafer at a close but safe (i.e., close to the surface to promote good signal strength but far enough away to minimize any possibility of impacting the wafer surface) distance, an appropriate sensor height must be calculated and set. Thus, the height of the sensor above the wafer surface must be measured and controlled to produce repeatable results. Furthermore, height control is also necessary to minimize the sensor height to improve resolution and signal strength. However, height is difficult to control and measure, as is the appropriate height for each specific wafer.

It is possible to use one of many commercially available height sensors to control the height of the nvCPD sensor above the wafer surface. This requires the expense of an additional sensor, and the added complexity of a calibration routine to determine the position of the nvCPD sensor tip relative to measurements made by the separate height sensor.

A related problem is the difficulty in establishing a point of reference for all distance measurements, including height, related to an nvCPD scan. A reference point is needed to produce useful measurement data for image production.

In some sensor systems, such as nvCPD sensors, it is necessary to separate the sharp peak signal from the other two components of the signal (low frequency signal and induced noise signals) to locate and measure the contaminated areas of a wafer. This is challenging because the sharp peak signal behaves like noise, i.e., it consists of sharp peaks that alternate their polarity in high frequency mode. Because of this, conventional high frequency filters based on the frequency domain only do not work, as they would degrade the sharp peak signal significantly along with the noise.

In addition, an nvCPD signal is generally delayed in time, which impacts on the quality of the nvCPD signal/image. As the sampling time increases, the time delay becomes larger. The time delay may be explained by the equivalent RC circuit modeling the electrical signal path from the probe tip to the output of the A/D converter through the amplifier, the data acquisition board and the connecting lines between them. The equivalent capacitance is mixed with the capacitance between the probe and the wafer surface, the parasitic capacitance of the connecting lines, the internal capacitance of the amplifier, and other known conventional effects. The result is that minute feature signals are less detectable, and the signal magnitude and thus the signal-to-noise ratio are smaller.

A critical need therefore exists for a fast, inexpensive, and effective means of detecting, locating, and classifying relatively small quantities of chemical content and physical features on wafers. In addition, there is a need for a system which minimizes cost and complexity of the sensor control mechanisms, such as height control. Furthermore, there is a need for methods and systems that have improved signal processing.

It is therefore an object of the invention to provide an improved method and system for inspection of surfaces of any materials, such as semiconductor wafers and other electronic devices.

It is an additional object of the invention to provide an improved method and system for providing images of surface defects on a semiconductor wafer or an integrated circuit device.

It is yet another object of the invention to provide an improved method and system for identifying different classes of wafer surface defects by pattern recognition.

It is still a further object of the invention to provide an improved method and system for classifying categories of surface defects on semiconductor wafers, including without limitation surface defect states, electrostatic field variations, oxide states and chemical contamination.

It is also an additional object of the invention to provide an improved method and system for sensing electrostatic fields arising from semiconductor wafer surface defects.

It is yet another object of the invention to provide an improved method and system for detecting the presence of thin dielectric films on surfaces of semiconductor wafers and to detect film defects such as pinholes, bubbles, delaminations, or contamination under the film.

It is a further object of the invention to provide an improved method and system to sense variations in oxide states on semiconductor wafer surfaces.

It is also a further object of the invention to provide an improved method and system to classify particulate contaminants on semiconductor wafers identified initially by optical inspection systems.

It is yet a further object of the invention to provide an improved method and system for detecting variations in dopant concentration of semiconductor wafers.

It is another object of the invention to provide an improved method and system for use of an nvCPD sensor to inspect the surface quality of semiconductor wafers.

It is still another object of the invention to provide an improved method and system of nvCPD sensors in combination with other inspection systems for evaluating semiconductor wafer surface properties.

It is a further object of the invention to provide an improved method and system for producing topological images of differing contact potential characteristic of defects on a semiconductor wafer.

It is also an object of the invention to provide an improved method and system for rapidly scanning the surface of a semiconductor wafer to identify sub-microscopic, microscopic and macroscopic surface defects characterized by potential field disturbances on the wafer surface.

It is also an object of the invention to provide an improved method and system for detecting the cleanliness of a semiconductor wafer to determine if a cleaning process has eliminated all contaminants and to avoid the time and expense of cleaning wafers for longer than is necessary to remove contaminants or to perform unnecessary processing steps.

In each case described above, wafer surface can refer to the front-side (patterned side) of the wafer, back-side (unpatterned side) of the wafer, or the edge of the wafer or any surface undergoing inspection regardless of the type of material.

Other objects, features and advantages of the present invention will be readily apparent from the following description of the preferred embodiment thereof, taken in conjunction with the accompanying drawings described below.

SUMMARY OF THE INVENTION

The present invention provides a wafer inspection system that is a fast, inexpensive, and effective means of detecting, locating, and classifying relatively small quantities of chemical content, and physical features on wafers, such as but not limited to semiconductor production, integrated circuit devices, or any material which may benefit from such inspections, while allowing for a minimization of the complexity of the sensor control mechanisms and an improvement in signal processing. In one preferred example embodiment, a wafer inspection system of the present invention includes steps for identifying a defect on a surface of a semiconductor wafer. In a preferred embodiment, the steps comprise providing a semiconductor wafer; providing a non-vibrating contact potential difference sensor; scanning the semiconductor wafer relative to the non-vibrating contact potential difference sensor; generating contact potential difference data from the non-vibrating sensor; and processing the non-vibrating contact potential difference sensor data to automatically detect a pattern that is characteristic of a particular type of defect.

In addition, the system of the present invention provides, in a preferred embodiment, a method for determining a reference point for the sensor. In addition, in some embodiments of the present invention the system includes a method for determining the height of the sensor. In addition, the present invention may preferably include a method for calculating the scan height to allow for wafer height variation. Furthermore, a system in accordance with the principles of the present invention preferably includes signal processing methods and devices for improving the native signal output of the sensor, such as by reducing noise or reducing signal time delay.

DETAILED DESCRIPTION OF THE PREFERRED EMBODIMENTS

Figure 1:
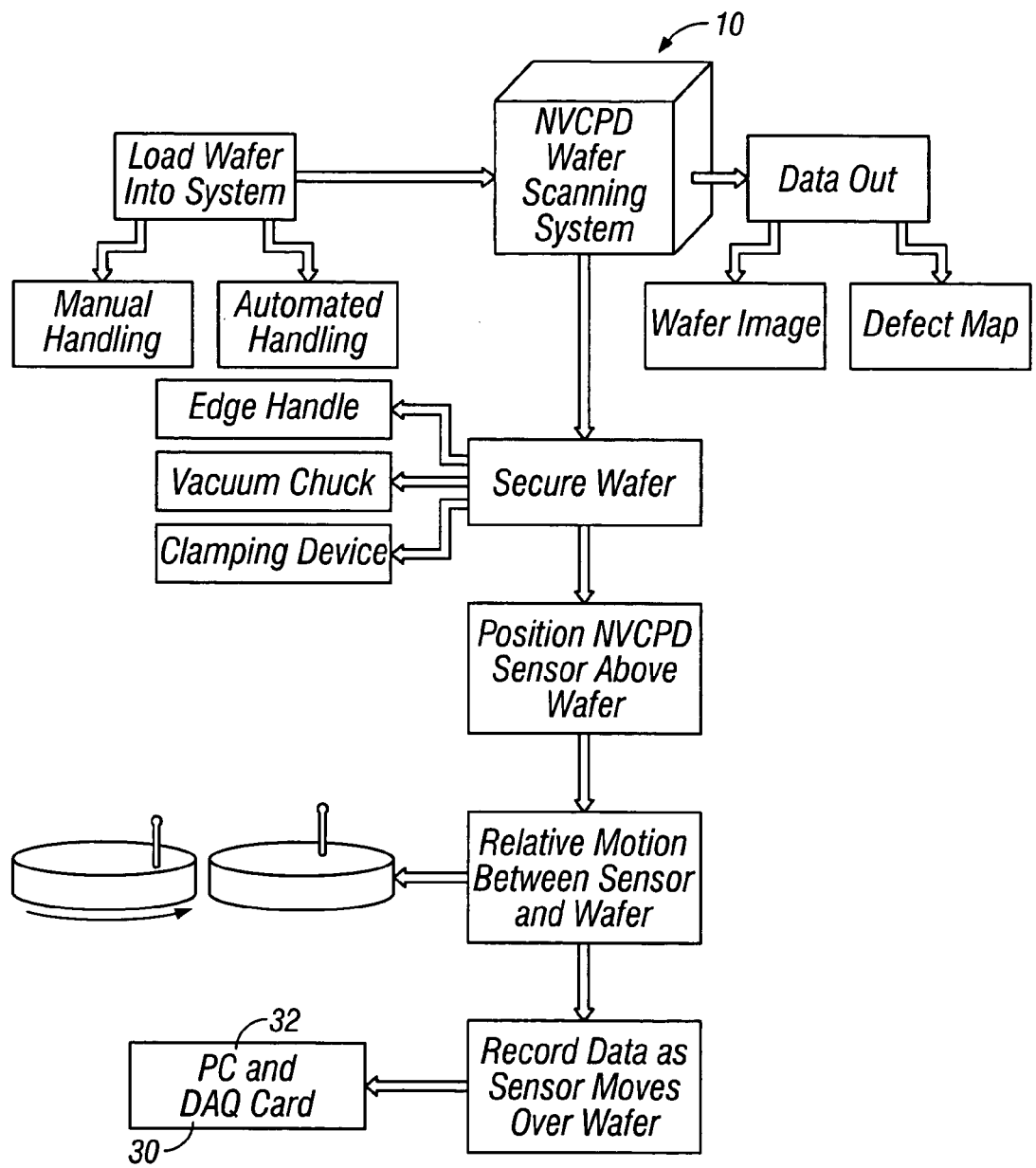
FIG. 1 illustrates one embodiment of the nvCPD scanning method and system.
Figure 2:
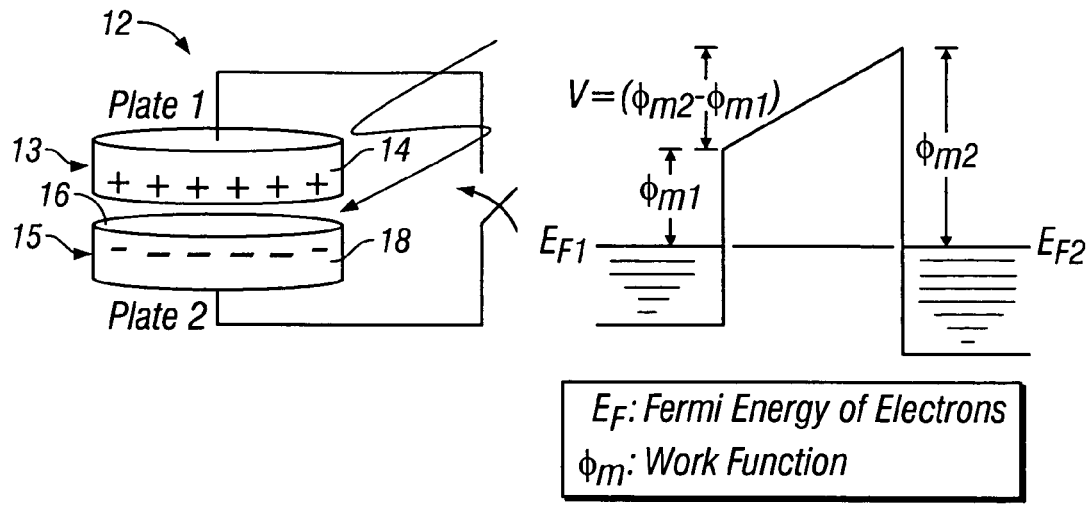
FIG. 2 illustrates the concept of the contact potential difference methodology.

A preferred embodiment of the invention is directed to an improved use of an nvCPD sensor. In particular, FIG. 1 illustrates a functional block flow diagram of components and operation of one preferred form of an nvCPD scanning system 10. A nvCPD sensor 12 (see FIG. 2) is based on the phenomena of contact potential difference which is a voltage generated between two dissimilar materials brought in close proximity to each other. An illustration of this concept can be seen in FIG. 2. In the case of the wafer scanning system 10, the sensor tip 13 forms a first plate 14 and a wafer 15 having a wafer surface 16 forms a second plate 18 (see FIG. 2.) Probe tip surface 20 of the first plate 14 is made of a conducting material with a fixed work function—generally, the difference in energy between the Fermi level of the solid and the free energy of the space outside the solid, including, in metals, the image potential of electrons just outside the surface. The wafer surface 16 of the second plate 18 has a work function which can vary due to irregularities in the semiconductor wafer surface 16 or contaminants or other materials deposited on the wafer surface 16. When the first plate 14 and the second plate 18 are electrically connected, the Fermi levels of the respective surface equilibrate and form an electric field between them. If the work function of the sensor tip 13 is fixed, the magnitude of the electric field is then related to the distance between the first plate 14 and the second plate 18, the relative dielectric between the first plate 14 and the second plate 18 and the work function of the wafer surface 16. In practice the first plate 14 and the second plate 18 equilibrate rapidly providing little to measure. To provide a current flow that can be measured, some motion of the sensor tip 12 relative to the wafer surface 16 must be realized. In one embodiment, the nvCPD sensor 12 is moved over the surface at a substantially fixed distance and variations in the wafer surface 16 cause a current to flow.

Figure 3:
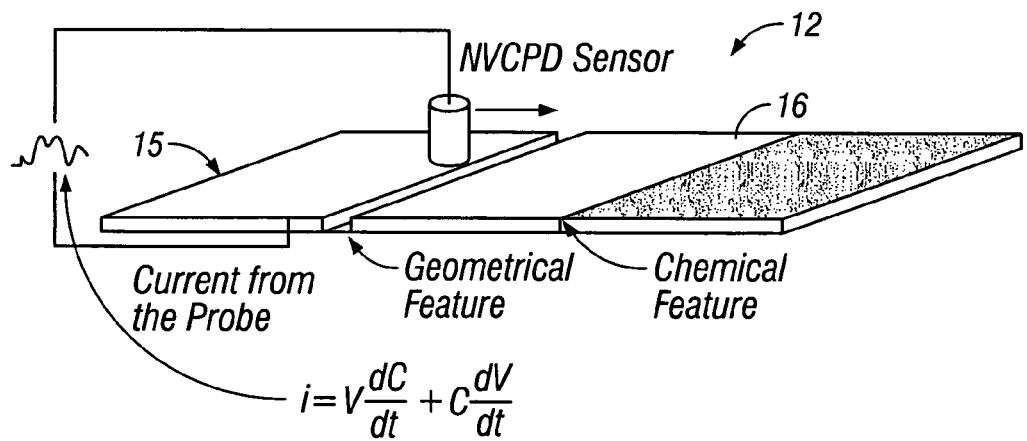
FIG. 3 illustrates an nvCPD scanning method.

An illustration of this concept can be seen in FIG. 3. The current flow from this nvCPD sensor 12 can be modeled by the following equation:

$$i = C\frac{\partial V}{\partial t} + V\frac{\partial C}{\partial t}$$

wherein C and V are defined as $$C = \frac{\varepsilon_o \varepsilon_r A}{d} \quad \text{and} \quad V = \frac{\Phi_{probe} - \Phi_{wafer}}{|e|}$$

and further wherein $\varepsilon_o$ is the permittivity of free space, $\varepsilon_r$ is the relative dielectric constant, A is the area of the probe tip, d is the distance between the sensor tip 13 and the wafer 15, $\Phi$ is the work function of the respective surface, and e is the charge on an electron. The V term can also be described as a difference in surface potentials between the nvCPD sensor 12 and the wafer 15. In addition the surface potentials on the wafer surface 16 can vary due to defects. The overall surface potential is related to the underlying materials work function but it can also be affected by adsorbed layers of material on the wafer surface 16. Even sub mono-layers of materials are known to significantly affect the surface potential.

Figure 4:
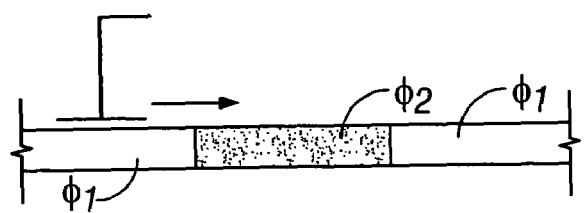
FIG. 4 illustrates the current output of an nvCPD probe as it passes over a positive and negative work function transition.
Figure 4:
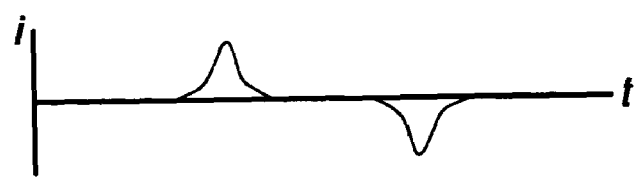

The $$C\frac{\partial V}{\partial t} \approx C\frac{\Phi probe - \Phi wafer}{\Delta t}$$

term is related to changes in work function on the wafer surface 16. It can be seen that the magnitude of this term is related to the relative changes in work function on the wafer surface 16 and relative speed at which the nvCPD sensor 12 is moved over the wafer surface 16. An illustration of the signal generated from this can be seen in FIG. 4. Thus, a system in accordance with the principles of the present invention is capable of generating one-dimensional signals and two-dimensional images, although three-dimensional images can be generated.

Many defects can present themselves as variations in the wafer work function or the overall surface potential. Both chemical and physical (i.e., geographical) features of the wafer surface and the underlying materials can affect the work function of a particular portion or even a single point on the wafer surface; thus, these features can be detected by a sensor in accordance with the principles of the present invention. For instance, variation in semiconductor dopant concentrations in the wafer 15 will cause varying characteristic work functions. In addition, other materials that could diffuse into the wafer 15, such as but not limited to copper, will cause variations in work function. Within the semiconductor material (or any other material susceptible to measurement) itself, mechanical phenomena such as dislocation pile-ups, cracks, and scratches generate local stresses which will change the local work function. In addition, adsorbed layers of atomic or molecular contaminants even at the sub monolayer level will generate appreciable surface potential variations. Particles deposited on the wafer 16 with a surface potential different than the surrounding wafer material will also create a signal. Layers of chemicals commonly used in the wafer fabrication process will affect the surface potential of the wafer. For instance residual CMP slurry or photo-resist would cause local variations in surface potential detectable by the nvCPD sensor 12 of the present invention. Such defects and chemistry have associated with them characteristic signatures which enable inspection of the wafer surface.

The $$V\frac{\partial C}{\partial t}$$

term is related to changes in gap between the nvCPD sensor 12 and the wafer 15 or variations in the relative dielectric constant. Geometrical imperfections in the wafer surface 16 or particles on the wafer surface 16 would manifest themselves in this component. Also because of its differential nature, the magnitude of this component would also increase as the relative speed of the nvCPD sensor 12 to the wafer 15 is increased.

As previously mentioned, physical or geographical aspects and defects can be imaged using a system in accordance with the principles of the present invention. Many classes of wafer defects would appear as geometrical changes in the wafer surface 16. In the wafer 15 itself, surface cracks, scratches, etched trenches, etc. would be nonlimiting examples of such defects causing a geometrical change in the wafer surface and an attendant change in the work function. In addition, particles deposited on the wafer 15 would also present themselves as a local change in the distance to the probe sensor tip 13.

Variations of dielectric films on the wafer 15 can also be detected. An example would be detecting variations in the oxide state grown on the silicon substrate (i.e. SiO, $SiO_2$, $SiO_3$, $SiO_4$). In addition, variations in dielectric of other non-conducting materials commonly deposited on the wafer could be detected.

It should also be noted that many features could present themselves as combinations of geometrical changes and chemical changes. For instance, a particle deposited on the wafer 15 of differing material than the underlying wafer 15 could cause variation. Also, a crack in the surface would also induce stresses that would cause variations in local work function.

Figure 5:
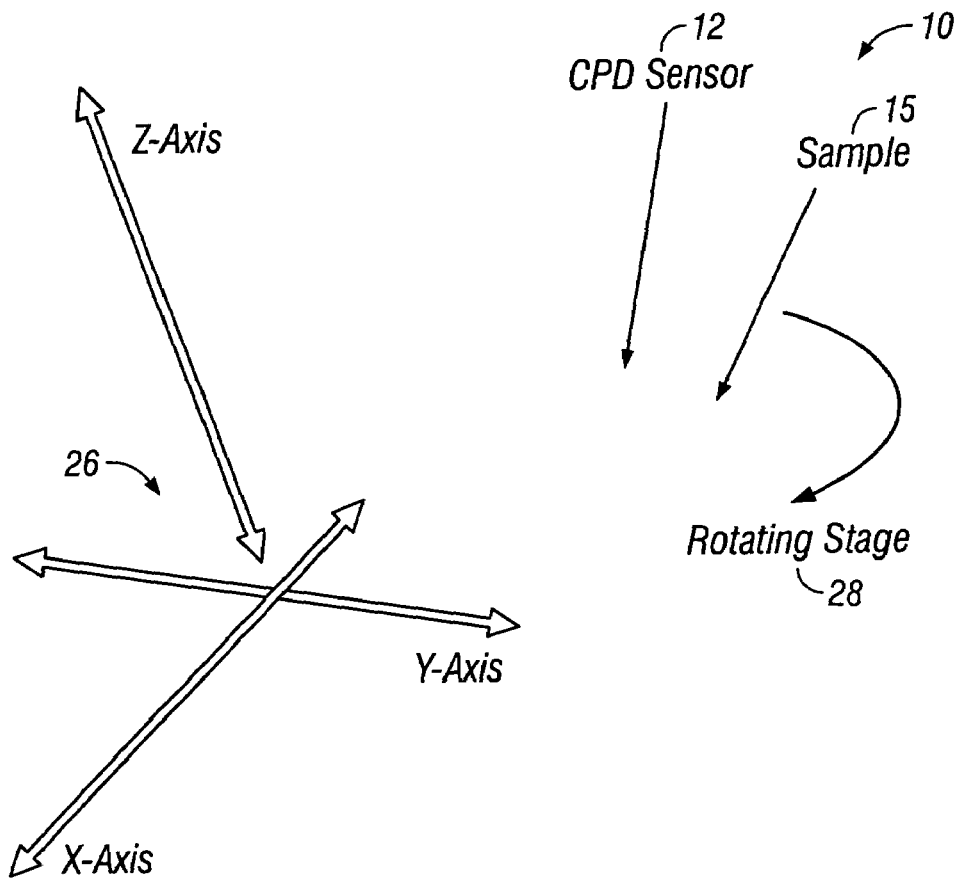
FIG. 5 illustrates axial orientation of the nvCPD system.
Figure 8A:
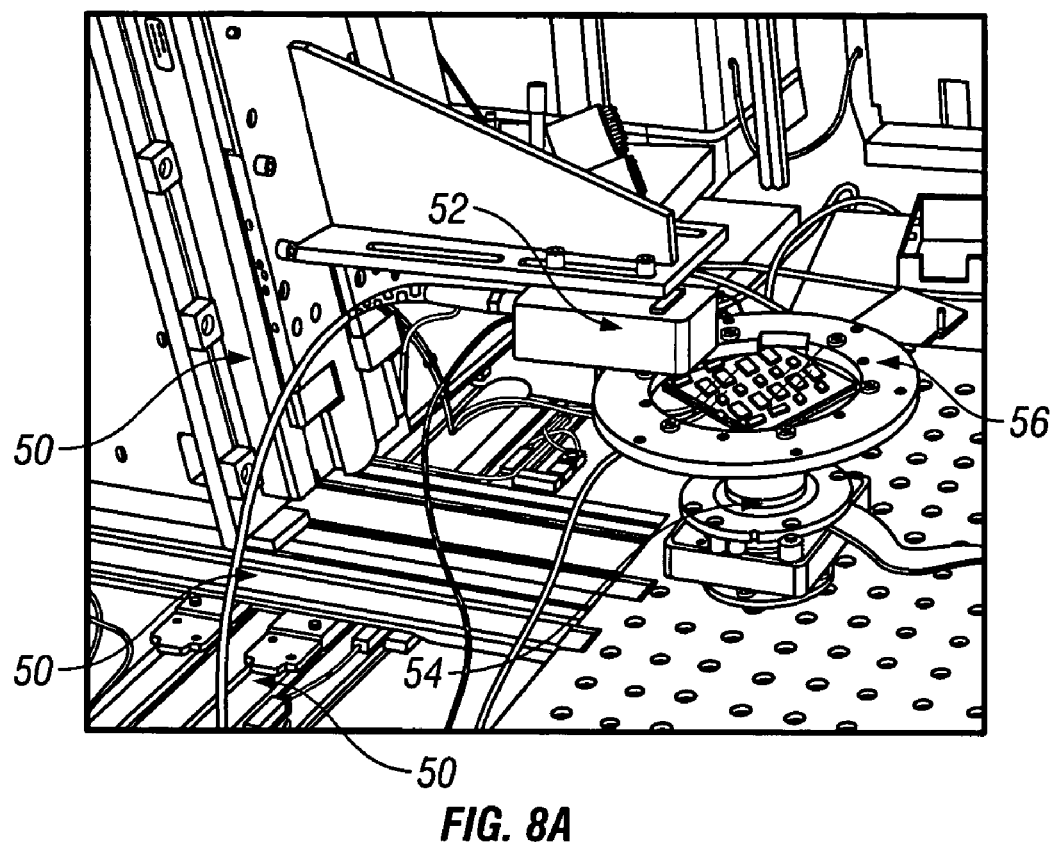
FIG. 8A illustrates one form of scanning nvCPD system with a three axis linear positioning system with the nvCPD sensor and a wafer mounted on a high speed spindle.
Figure 8B:
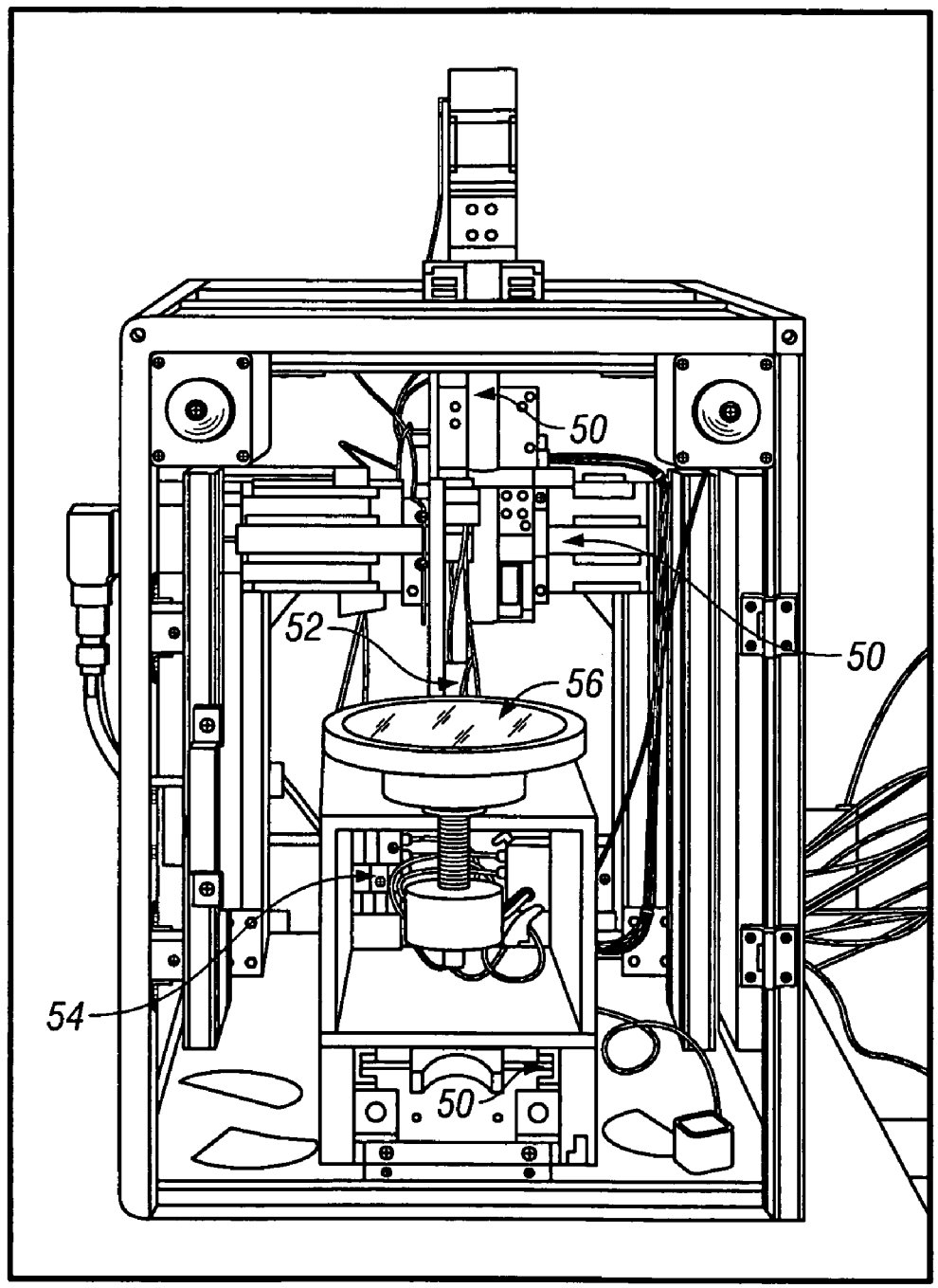
FIG. 8B illustrates another form of scanning nvCPD system.

In FIG. 5 is schematically shown one form of the system 10 for application of the nvCPD sensor 12 to scan the wafer 15 for defects and contamination. FIGS. 8A and 8B also illustrate more detailed drawings of two alternative operating embodiments of the system 10. The system 10 in FIG. 5 includes an X-Y-Z positioning system 26, a rotating wafer stage 28, a high speed data acquisition system 30 with a personal computer (PC) 32, and control software executed by the PC 32.

Figure 21A:
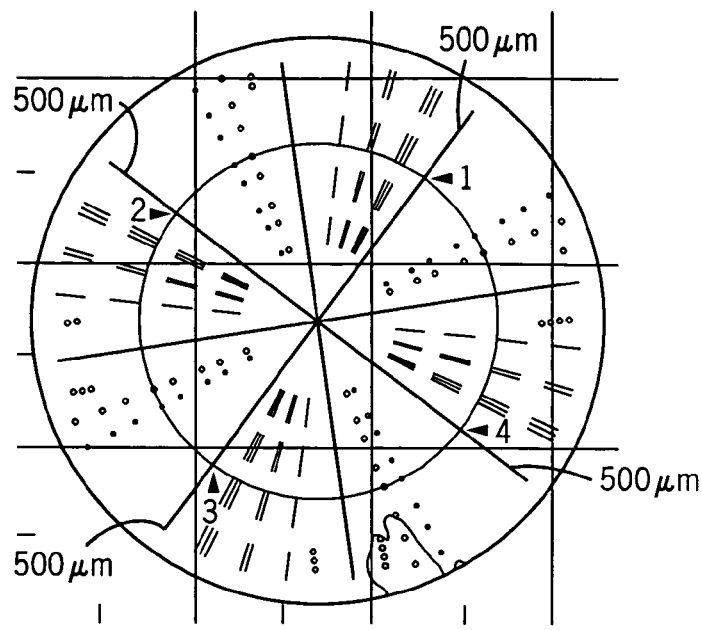
FIG. 21A illustrates a wafer map produced in accordance with the principles of the present invention, wherein the wafer pattern is one atomic layer thick over native silicon oxide.
Figure 21C:
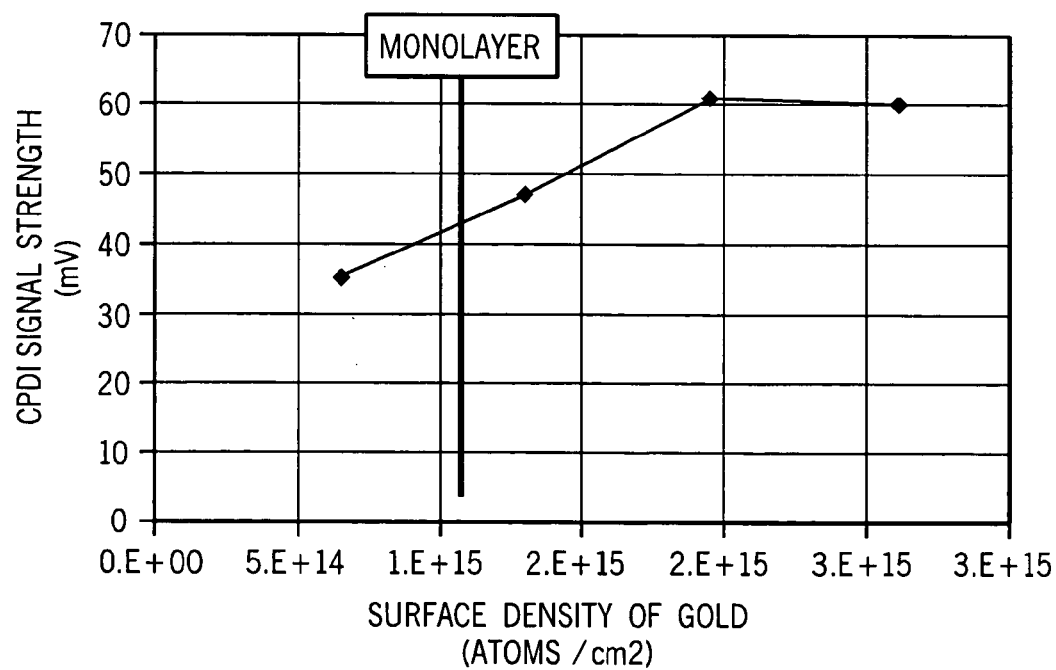
FIG. 21C is a graph of the signal strength versus the density of gold for the wafer map depicted in FIG. 21A.
Figure 21B:
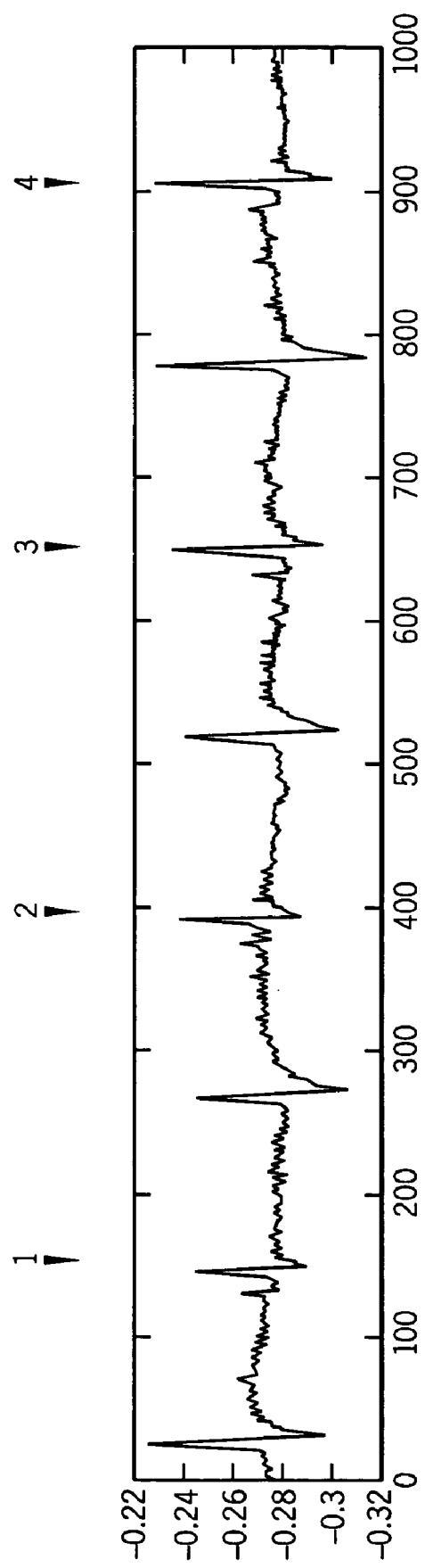
FIG. 21B is a graph showing signal strength along a single probe track.

As shown in more detail in FIG. 8A, in one embodiment, the wafer 15 is affixed to a rotating spindle or chuck 54 (see FIG. 1) using a clamping fixture 56 on the wafer edges. A sensor positioning system 50 includes an nvCPD sensor 52 positioned a fixed distance from the wafer 15 is mounted to a spindle 54. The wafer 15 (not seen in this view) is then rotated at high speed, and the nvCPD sensor 52 is translated radially to collect data in circumferential tracks. The scanning procedure as shown schematically in FIG. 9 lasts between a few seconds and several minutes, depending on the number of scanned tracks, the speed of the spindle 54, and the speed of the sensor positioning system 52. The tracks of data are then put together to form a CPD image. These CPD images allow the visualization of chemical and geometrical defects and thereby enable classification of the type of defect present on the wafer surface. Some examples of these CPD images can be seen in FIG. 10A-15 and are taken from a 100 mm wafer compared with optical images of the same wafer (see, Example infra). The present invention is capable of generating image maps of one atomic layer thick patterns, as shown in FIG. 21A. FIG. 21B illustrates the signal strength as the wafer is rotated relative to the probe, thus passing over defects and features of the wafer surface. As shown in FIG. 21C, the present invention, in fact, detected sputtered gold at densities less than a single atomic layer.

Figure 6:
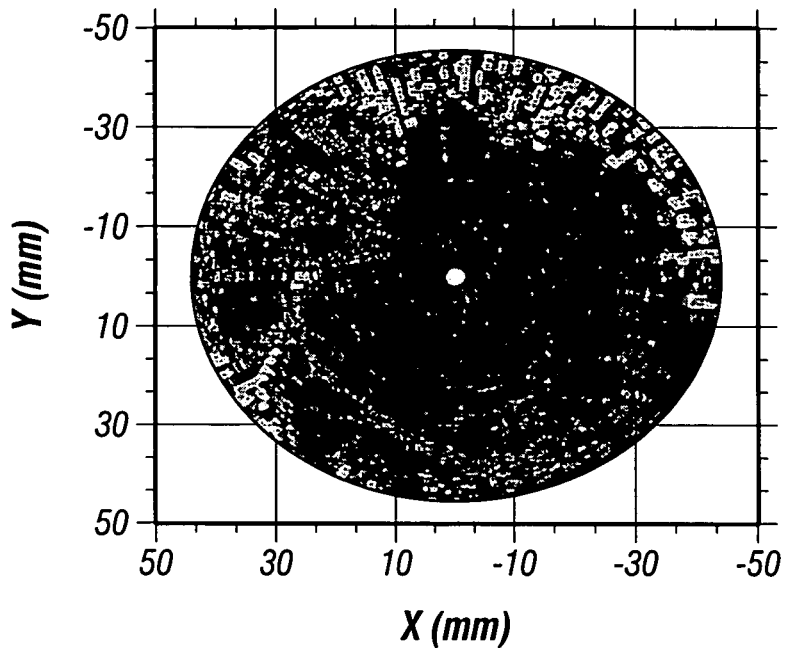
FIG. 6 illustrates standard deviation of signals within a scan area.
Figure 9:
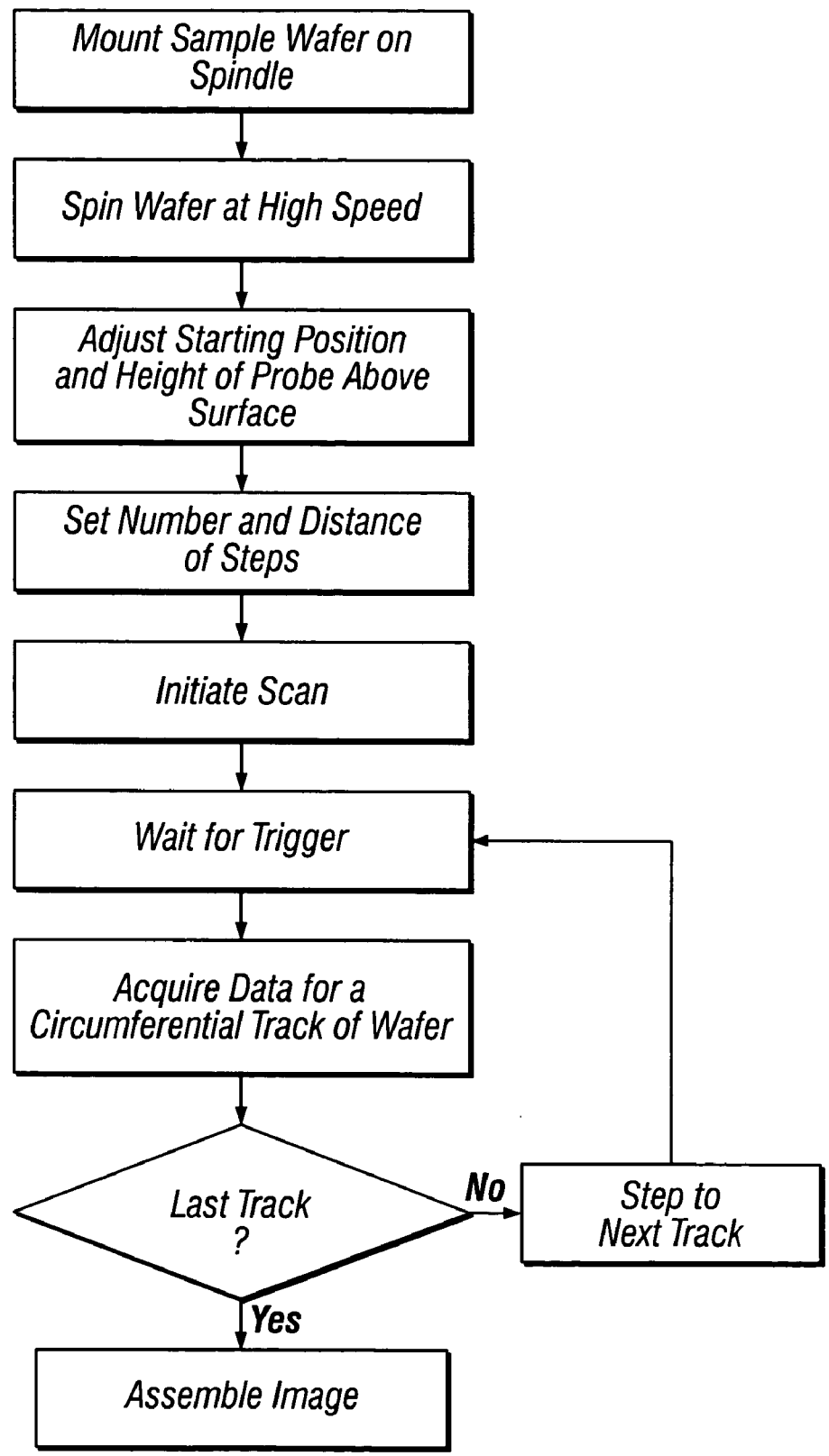
FIG. 9 illustrates a flow diagram for the image acquisition process of a radially scanned nvCPD imaging system.

The images generated by the scanning procedure of FIG. 9 were subsequently processed to automatically locate defects; thus locating areas of high variability. An ideal surface would exhibit a flat signal, but a wafer surface with defects would exhibit some variability in the signal. To locate areas with defects, the data was broken up in to small areas of known location. The standard deviation of the signal within these areas was determined. Areas with defects showed a higher standard deviation, and these results can be seen in FIG. 6. Areas with defects appear brighter than lower variability areas of the wafer 15. This is one of many possible methods in accordance with the principles of the present invention to process the sensor data.

More generally, a defect can be identified by one or more of the following:

Process the data to look for a voltage or change in voltage (or pattern of voltages or changes in voltages) that exceeds some user-defined value (threshold).

Compare the data to a known pattern that represents a defect via some form of correlation or template matching.

Convert the spatial data to the frequency domain and then identify peaks in the frequency domain that represent defects with unique spatial characteristics.

These techniques can also be combined with other techniques to yield analytical results. The signal may also be preprocessed to facilitate defect detection, such as, for example:

Since the signal is differential, it can be integrated over some distance to produce voltages that represent relative CPD's over the surface of the wafer 15.

If the wafer 15 is "patterned", then this known pattern can be removed from the data prior to processing. This would likely be accomplished through some conventional method of variation of image or signal subtraction in either the space or frequency domains.

The signal would likely be processed with some form of frequency filtering to remove high or low frequencies depending on the size, shape and other characteristics of the expected defects.

The signal could be processed to remove features of a certain size by doing what is called "morphological processing" which is well known in the art.

Figure 22A:
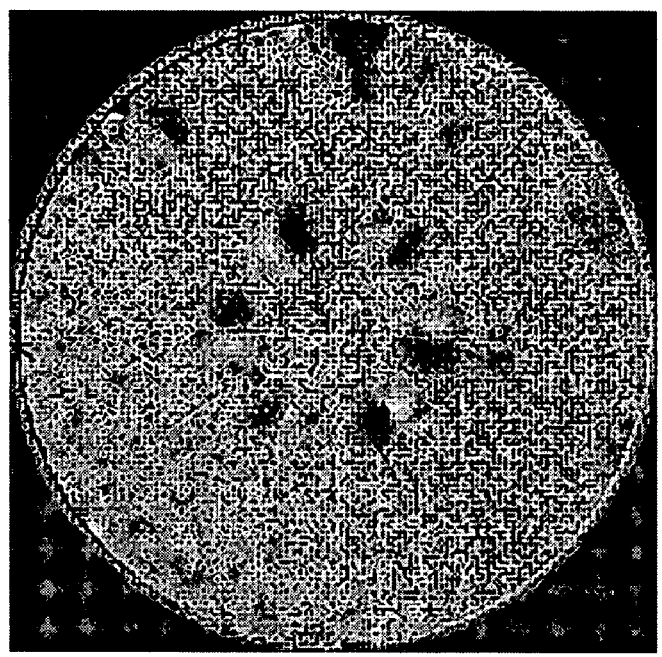
FIG. 22A is a 2D Edge Detection optical view using Canny Algorithm at Multiple Resolutions (#7 Wafer dipped into a CMP Slurry)
Figure 22B:
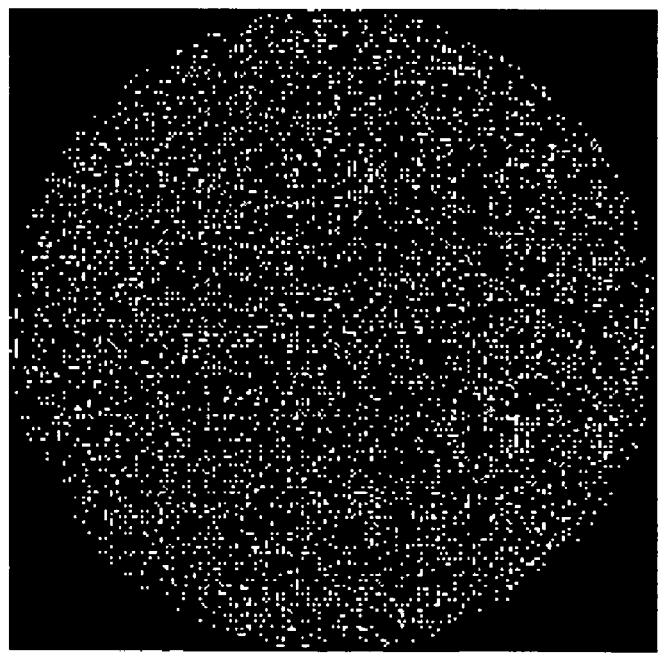
FIG. 22B is a 2D Edge Detection image produced in accordance with the principles of the present invention using Canny Algorithm at Multiple Resolutions (#7 Wafer dipped into a CMP Slurry, threshold=0.00001, Contamination Level=24.5)
Figure 22C:
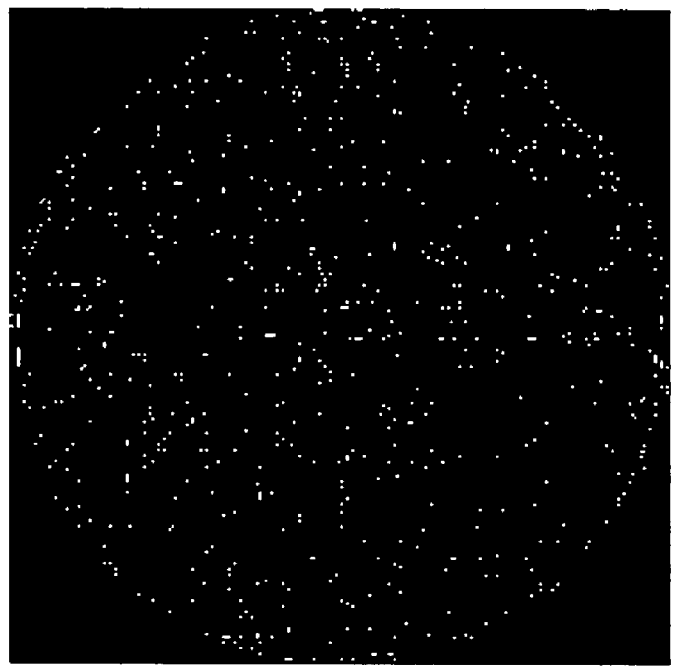
FIG. 22C is a 2D Edge Detection image produced in accordance with the principles of the present invention using Canny Algorithm at Multiple Resolutions (#7 Wafer dipped into a CMP Slurry, threshold=0.008, Contamination Level=4.5)
Figure 22D:
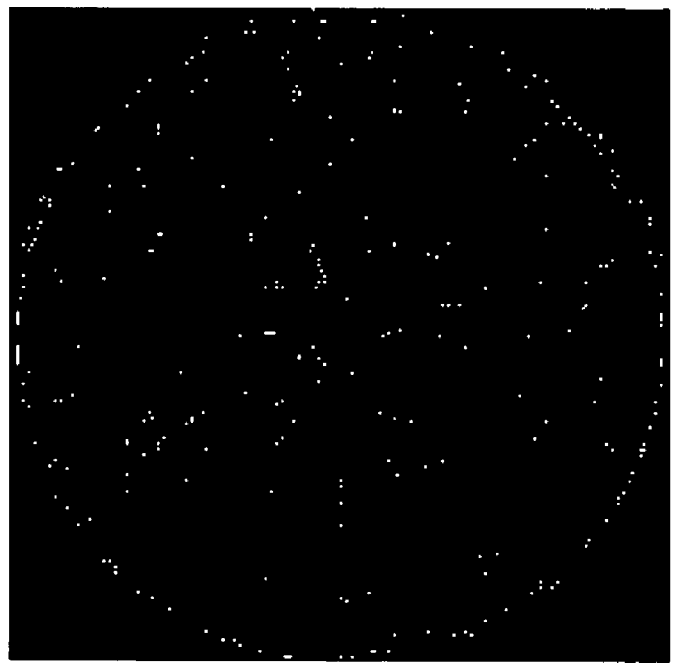
FIG. 22D is a 2D Edge Detection image produced in accordance with the principles of the present invention using Canny Algorithm at Multiple Resolutions (#7 Wafer dipped into a CMP Slurry, threshold=0.01, Contamination Level=1.9)
Figure 22E:
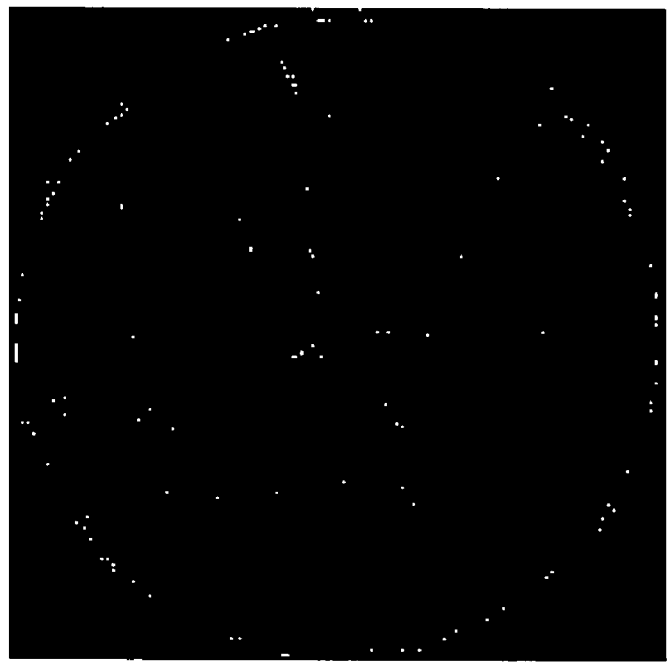
FIG. 22E is a 2D Edge Detection image produced in accordance with the principles of the present invention using Canny Algorithm at Multiple Resolutions (#7 Wafer dipped into a CMP Slurry, threshold=0.012, Contamination Level=1.1)
Figure 22F:
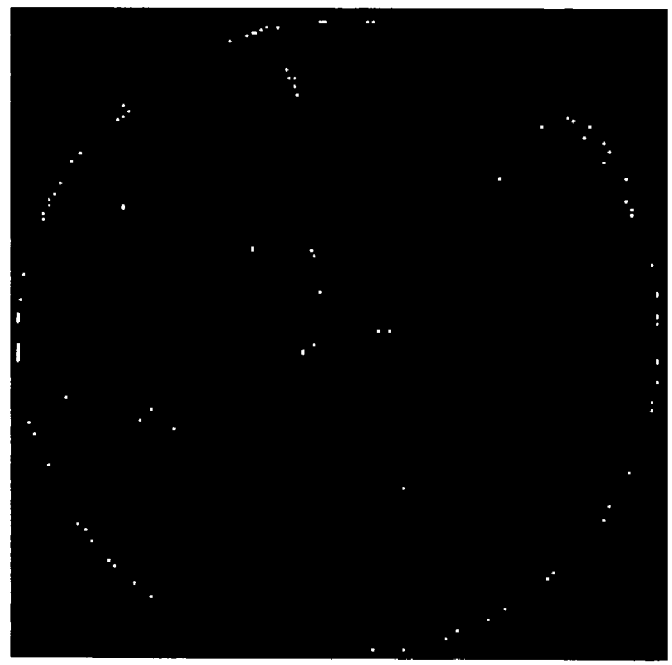
FIG. 22F is a 2D Edge Detection image produced in accordance with the principles of the present invention using Canny Algorithm at Multiple Resolutions (#7 Wafer dipped into a CMP Slurry, threshold=0.014, Contamination Level=0.8)
Figure 23A:
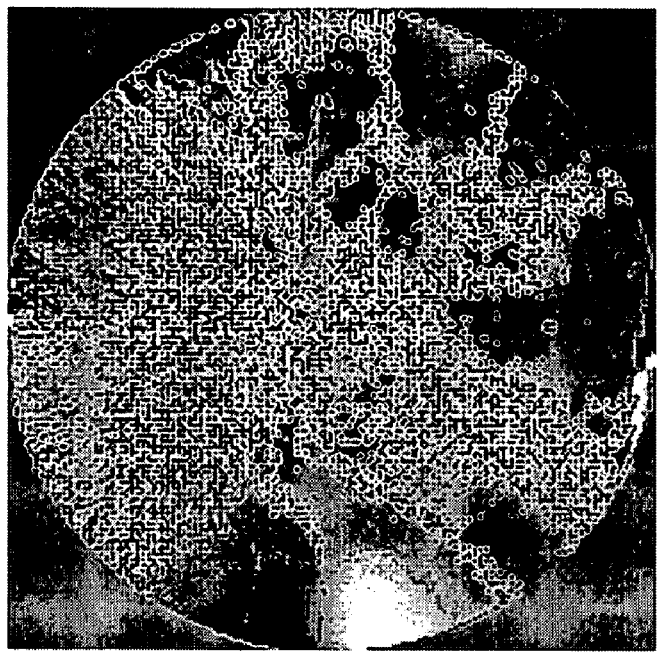
FIG. 23A an optical image of 2D Edge Detection produced in accordance with the principles of the present invention using Canny Algorithm at Different Scales (Qcept #6 Wafer dipped into a CMP Slurry)
Figure 23B:
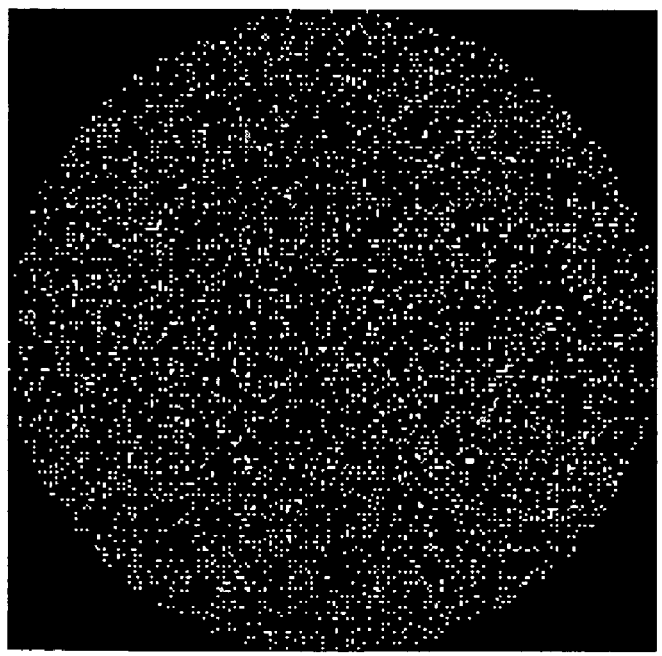
FIG. 23B an optical image of 2D Edge Detection produced in accordance with the principles of the present invention using Canny Algorithm at Different Scales (Qcept #6 Wafer dipped into a CMP Slurry, threshold=0.00001, Contamination Level=24.3)
Figure 23C:
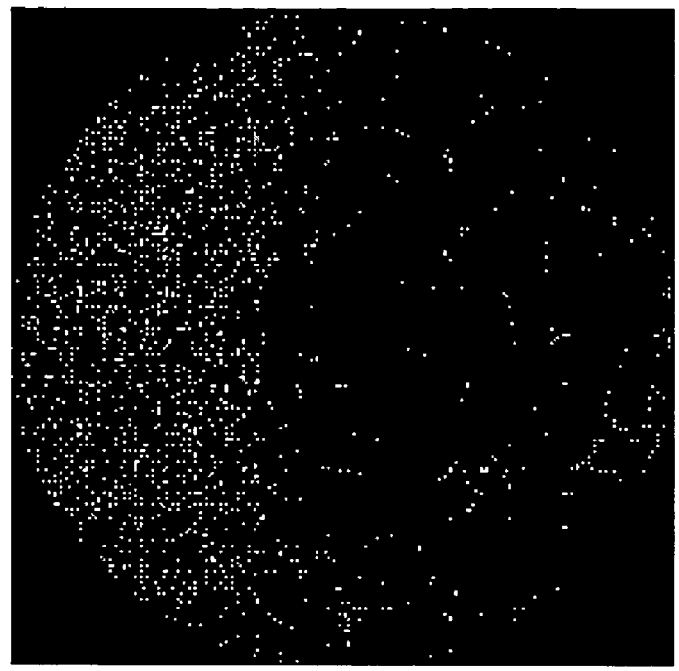
FIG. 23C an optical image of 2D Edge Detection produced in accordance with the principles of the present invention using Canny Algorithm at Different Scales (Qcept #6 Wafer dipped into a CMP Slurry, threshold=0.005, Contamination Level=9.6)
Figure 23D:
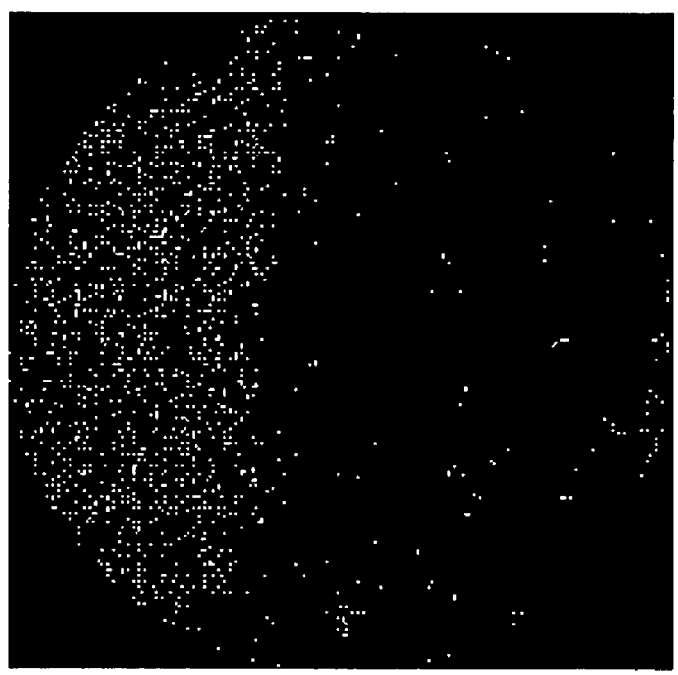
FIG. 23D an optical image of 2D Edge Detection produced in accordance with the principles of the present invention using Canny Algorithm at Different Scales (Qcept #6 Wafer dipped into a CMP Slurry, threshold=0.006, Contamination Level=8.2)
Figure 23E:
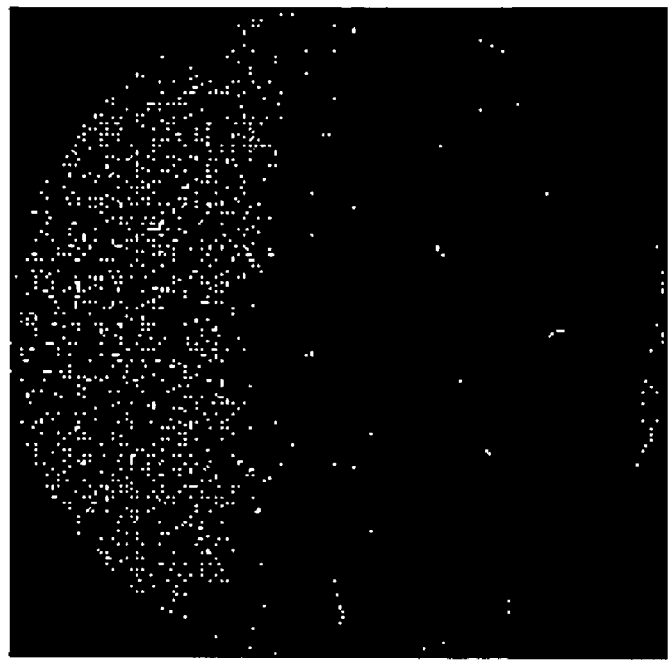
FIG. 23E an optical image of 2D Edge Detection produced in accordance with the principles of the present invention using Canny Algorithm at Different Scales (Qcept #6 Wafer dipped into a CMP Slurry, threshold=0.008, Contamination Level=6.9)
Figure 23F:
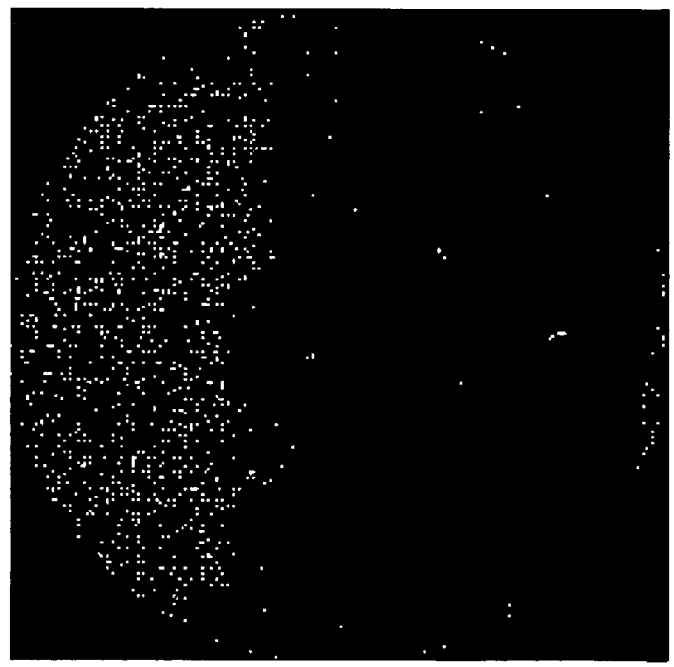
FIG. 23F an optical image of 2D Edge Detection produced in accordance with the principles of the present invention using Canny Algorithm at Different Scales (Qcept #6 Wafer dipped into a CMP Slurry, threshold=0.009, Contamination Level=6.4).

In one embodiment, a defect is detected and the contamination level is quantified based on an edge detection algorithm, such as but not limited to Canny Edge detection algorithm. Multiple resolutions may be used or multiple scales or a combination thereof. FIGS. 22B-F depict the edge detection at various resolutions and in comparison to an optical image (FIG. 22A). FIGS. 23B-F depict edge detection at various scales and in comparison to an optical image (FIG. 23A). In a preferred example of such an embodiment, the contamination is detected and quantified using the steps of:

Generating a CPD sensor peak signal at the boundary between two different areas (The peak signals behave much like the "edges", an image processing term. So, the contaminated area can be located by edge detection.);

Apply an Edge detection algorithm (such as the 2D Canny algorithm);

Multiple resolutions with different thresholds (thereby enabling detection of various size of contaminants, i.e. the higher resolution (lower threshold) will find the smaller contaminants);

Quantifying contamination level (CL) by the edge area over the total wafer area in the simplest way.

As previously discussed, determining a reference point for the sensor is necessary for optimal results. In one embodiment, the reference point is at the center of rotation (in the X-Y plane) and at the height of the surface of the wafer (on the Z axis). To find this point, the center of rotation and the height of the surface of the wafer must be determined, and then the height sensor is correlated with the Z position of the nvCPD sensor.

To find the center of rotation, the nvCPD sensor and motion system are used to find a geometrical or chemical feature on the surface of the spinning wafer at three or more points. Since the wafer is spinning, the feature describes a circle. The center of the circle is the center of rotation. Given the coordinates of three distinct points $(A(x_1,y_1), B(x_2,y_2),$ and $C(x,y))$ on the diameter of the defined circle on the circle, its center is found algebraically by the equation:

$$(x-x_1)(x-x_2)+(y-y_1)(y-y_2)=0.$$

Due to slight measurement errors, a different set of points might yield slightly different center coordinates. The "true" center of rotation is deemed to be the locus (average) of these points.

In one embodiment, to find the height of the surface of the wafer without touching the wafer surface, two sensors, the nvCPD sensor and a height sensor (which could itself be an nvCPD sensor in an embodiment discussed below) can be used. The nvCPD sensor and height sensor are calibrated so that when a reading is taken with the height sensor, the Z-axis coordinate of the tip of the nvCPD sensor is ascertained. (This calibration procedure is described below.) At that point, the readings of the height sensor are correlated with the Z position of the nvCPD sensor. Thereafter, the height sensor is used to detect the position of the surface of the wafer without touching it and then the tip of the nvCPD sensor positioned accordingly.

In one embodiment, the height sensor is correlated with the Z position of the nvCPD sensor based on two assumptions: first, that within its usable range, measurements from the height sensor are linear in the Z axis and that a constant, k, can map changes in height measurements to proportional changes in Z; and second, that the relative positions of the height sensor and nvCPD sensor are fixed, i.e. the two sensors can move relative to the rest of the world but only as a unit; they, therefore, cannot move independently. Based on these assumptions, a point, P, is picked in the X-Y plane where calibration is to be performed. The height sensor is positioned above P, and a measurement from the height sensor, Hm, correlated with a coordinate on the Z axis, Zh. Next the nvCPD sensor is positioned above P and move it down until it touches at a point, Zc. The nvCPD signal changes significantly when the sensor tip touches the surface. Once these values are known, the Z value of the point where the tip of the nvCPD sensor would touch the surface is derived with the following equation:

$$Z_{surface}=Z_{current}+Z_c-Z_h+(H_m-H_{current})/k$$

wherein:

$Z_{surface}$ is the height of the surface where the tip of the nvCPD sensor would touch $Z_{current}$ is the current height of the sensor $H_{current}$ is the current height sensor measurement As previously mentioned, the height of the sensor should be measured and controlled to produce repeatable results. It is also possible to use an nvCPD sensor to control the height in a semiconductor wafer inspection system in accordance with the principles of the present invention. In order to use the nvCPD sensor to control height, the system must provide the capability to apply a time-varying bias voltage between the probe tip and the wafer surface. As the bias voltage varies, it produces an output signal that is a function of the capacitance between the probe tip and the wafer surface. The closer the probe tip is to the surface, the larger the output voltage. After the relationship between height and capacitance is determined, the magnitude of the output signal can be used to calculate the height of the sensor. The signal magnitude can be calculated as the peak-to-peak, standard deviation, RMS, or some other measure known in the art.

Again, the formula for the output of the nvCPD sensor is:

$$i = C\frac{\partial V}{\partial t} + V\frac{\partial C}{\partial t}$$

The voltage V is the contact potential difference between the probe tip and the wafer surface. If a bias voltage is applied, the formula then becomes:

$$i = C\frac{\partial (V+Vb)}{\partial t} + (V+Vb)\frac{\partial C}{\partial t}$$

where Vb is the bias voltage. If the nvCPD sensor is not moving relative to the surface of the wafer (or is moving relatively slowly), then the capacitance C and the contact potential difference voltage V are not changing, and the equation becomes:

$$i = C\frac{\partial Vb}{\partial t}$$

Since the bias voltage is a known fixed frequency and magnitude, the output current is a function of the capacitance (C). C is a combination of the capacitance between the probe tip and wafer surface, and any stray capacitances in the circuit. The capacitance vs. height function can be characterized and used to determine the height of the nvCPD probe at a point above the wafer surface. Once the height of the sensor is determined, then the bias voltage can be turned off in order to make scanning nvCPD measurements.

Figure 18:
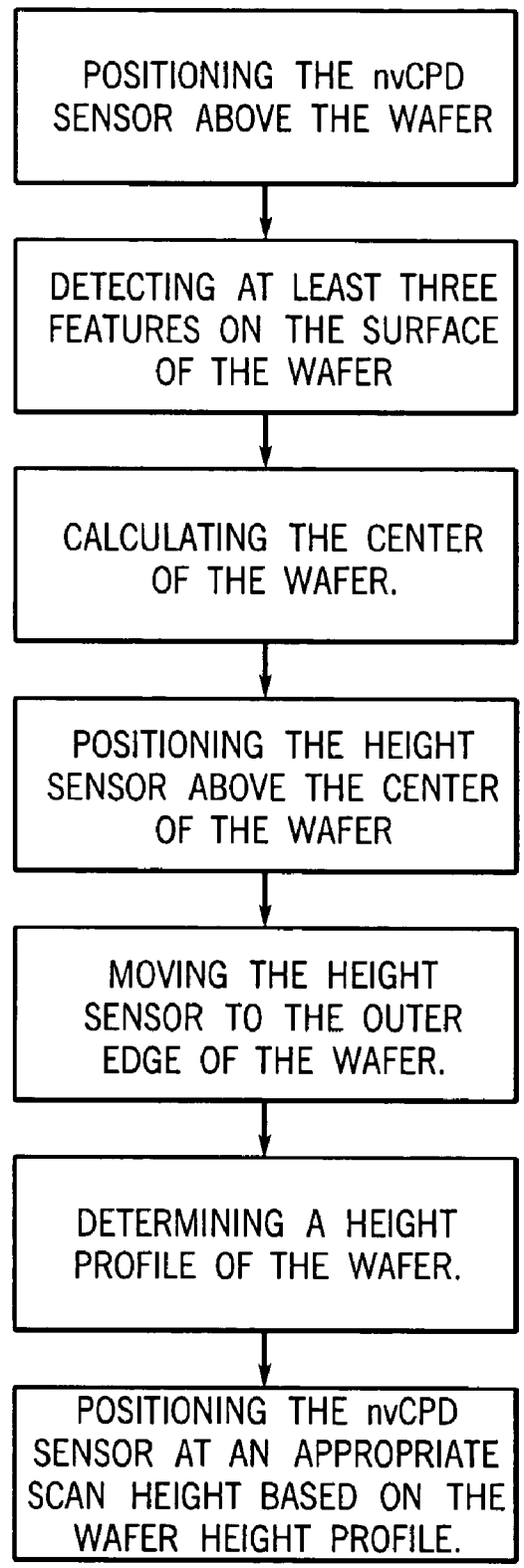
FIG. 18 is a detailed view of the Adjust Starting Position and Height of Probe Above Surface step of FIG. 9.

However, in some embodiments prior to scanning a portion of the wafer, a height profile is established with a height sensor and then the scanning height of the nvCPD sensor adjusted appropriately. FIG. 18 depicts one embodiment which utilizes a height profile of the wafer to position the sensor. The height profile is determined by first moving the height sensor to the center of rotation and then, with the wafer spinning, the height sensor is moved out toward the edge of the wafer until it senses the edge. Note that this also allows the diameter of the wafer to be determined. The sensor is then moved back toward the center until it is within the wafer flat(s) or notch. One or more height measurements taken along the way establish the profile. An appropriate height for nvCPD sensor scanning is calculated based on the profile, particularly based on the maximum detected height.

As mentioned above, often nvCPD sensors used in accordance with the principles of the present invention generate a peak signal that behaves like noise. In accordance with the principles of the present invention, denoising algorithms can be applied to both nvCPD signals and nvCPD images. In one embodiment, the nvCPD signal/image data are decomposed into the wavelet domain using one of the wavelets available such as but not limited to 'Coiflet', 'Daubechies', 'Symmlet', and other such wavelets. Then, as a result of the wavelet decomposition, a series of wavelet coefficients are obtained at a finite number of scales that can be given by the user. A coefficient at a particular scale represents the magnitude of the frequency corresponding to that scale at the point corresponding to that coefficient. The nvCPD signal/image can then be reconstructed by the coefficients in reverse order.

Figure 19:
FIG. 19 illustrates NCVPD processed wafer images before deconvolution.
Figure 20:
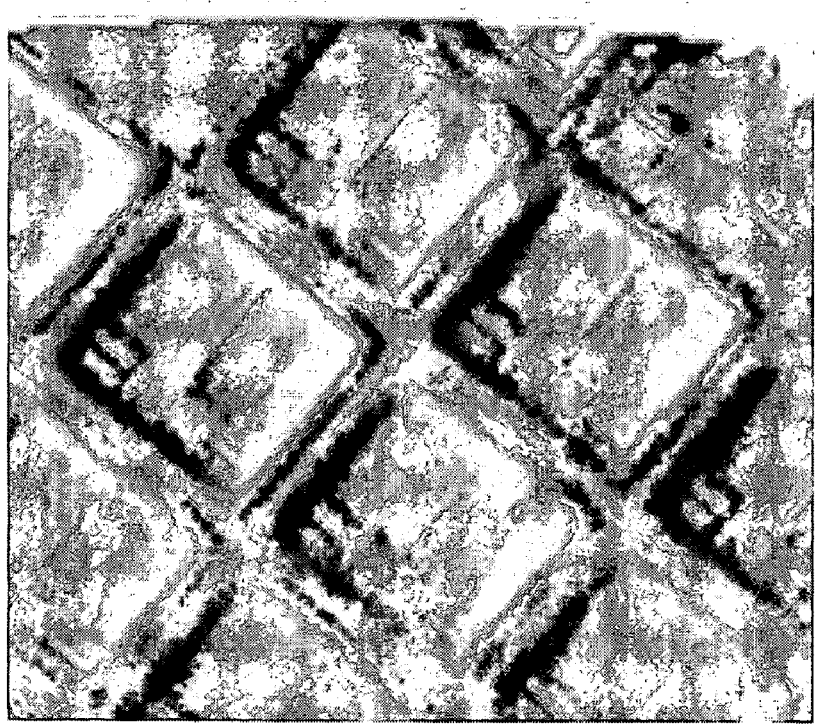
FIG. 20 illustrates NCVPD processed wafer images after deconvolution.

By adjusting the coefficients and performing reconstruction, the three components (peak, low frequency, and noise) of the nvCPD signal/image can be selectively filtered out. To eject the low frequency component from the nvCPD signal/image, only wavelet coefficients at fine scales are used for reconstruction since the low frequency component of the nvCPD signal/image are represented by the coefficients at coarse scales. To eject the noise from the nvCPD signal/image, the coefficients at fine scales can be shrunk softly based on the threshold given. The threshold can be determined using any one of numerous methods known in the art such as, but not limited to, 'Visu', 'SURE', 'Hybrid', 'MinMax'. The sharp peak signal that is related to contamination on the wafer can be reconstructed substantially in isolation by the wavelet coefficients resulting after the two processes above. Thus, noise such as vibrations or a wobbling of the wafer can be filtered out of the signal. FIG. 19 depicts an image produced by a system in accordance with the principles of the present invention without deconvoluting or denoising the data. FIG. 20 illustrates the improved resolution and definition of an image which is denoised in accordance with the principles of the preferred embodiment.

A semiconductor wafer inspection system in accordance with the principles of the present invention which utilizes a nvCPD sensor may, as discussed above, experience a time delay. However, the present invention provides a filtering technique to remove this time delay. First, the time delay circuit is modeled as a first order RC circuit. The continuous-time transfer function of the RC circuit is given by $$\frac{Y(s)}{X(s)} = \frac{1}{\tau s + 1}$$

where X(s) and Y(s) are the Laplace transformation of the input current signal at the probe tip and the output voltage measurement to the data acquisition, and T is the time delay constant.

The continuous current signal is fed into and amplified by the amplifier, and then converted into a discrete signal through the A/D converter. In this way, the collected data by the computer at the final stage is a series of discrete data. For digital signal processing, the continuous-time transfer function of the RC circuit is converted into a discrete-time transfer function based on Z-transformation. This discretized transfer function has the form $$\frac{Y(z)}{X(z)} = \frac{\alpha}{z + \beta}$$

wherein the constants α and β are determined by the discretization method employed, the sampling time and the time delay constant, τ.

Next, in a preferred embodiment, the impulse response of the discretized transfer function is determined. In general, the impulse response is a finite number of positive discrete values that converges to zero gradually. Once the impulse response is found, the deconvolution process with the impulse response is performed on each track data separately.

Figure 16:
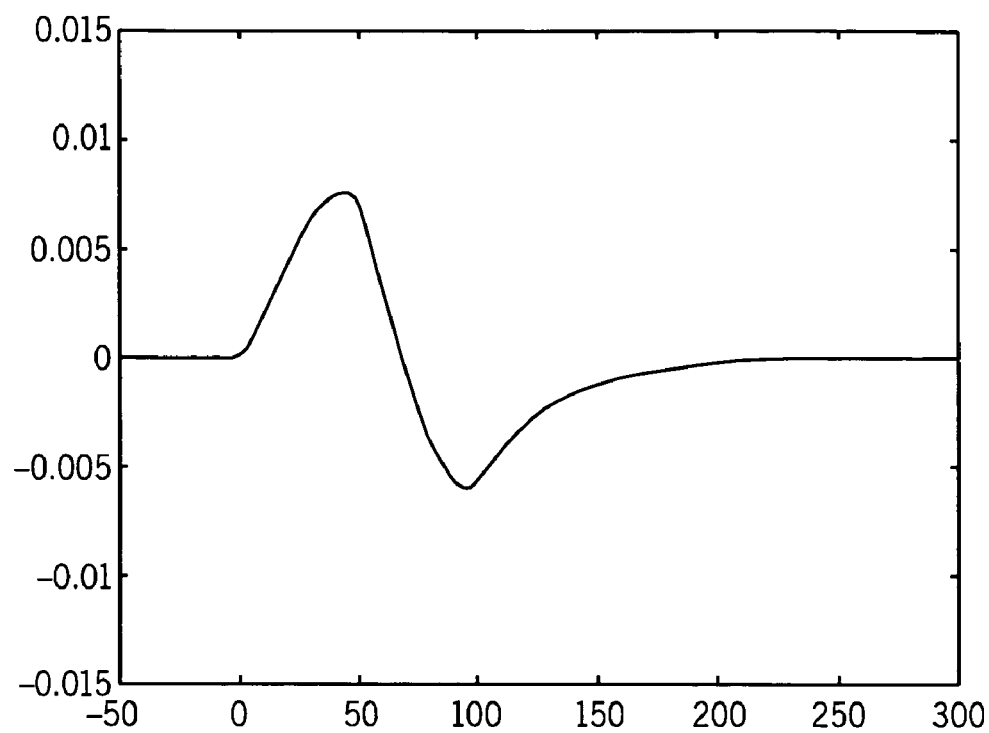
FIG. 16 illustrates a chart depicting a typical nvCPD signal where there is a set of peaks comprising a positive peak and a negative peak having non-equivalent heights.
Figure 17:
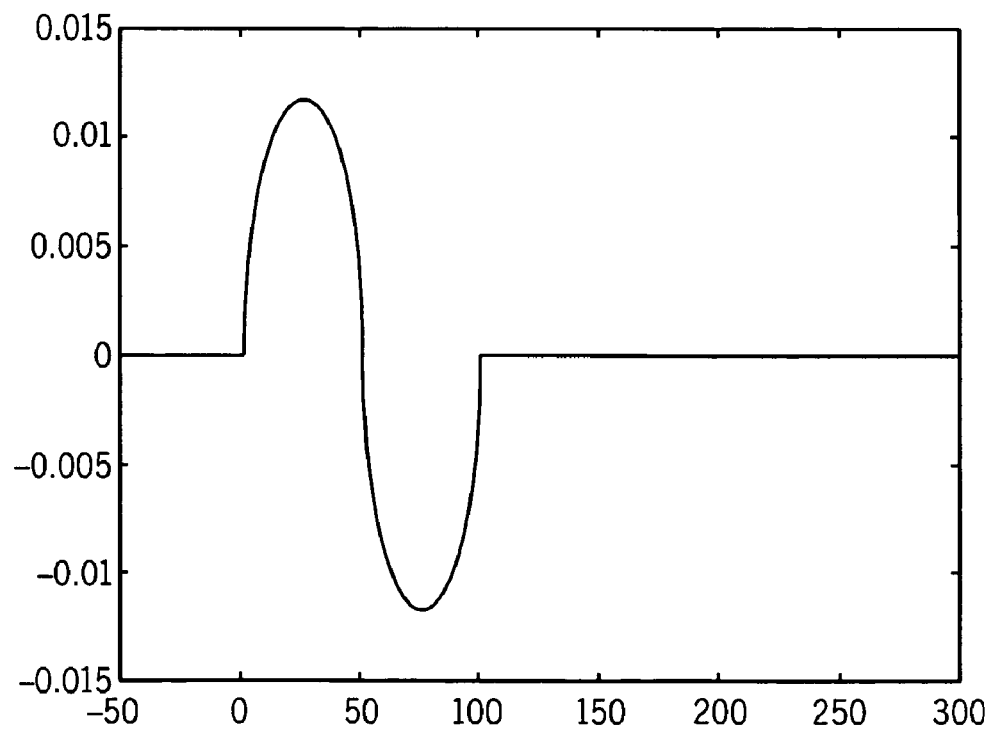
FIG. 17 illustrates a chart depicting a signal output of one embodiment of the present invention where the positive peak height is substantially equivalent to the negative peak height.

Time constant prediction is important and can be assessed by comparing the positive peak height and the negative peak height. FIG. 16 shows a typical nvCPD signal where there is a pair of a positive peak and a negative peak. It is shown that the positive peak is higher than the negative peak. With zero time delay, the signal would look like FIG. 17, where the positive peak height is equivalent to the negative peak height.

By comparing the positive peak height with negative peak height, the time constant can be estimated correctly. If the time constant is underestimated, the former peak (in this example, the positive peak) is higher than the latter peak (in this example, the negative peak). If the time constant is overestimated, the former peak is lower than the latter peak. By varying the time constant, a point when the positive and negative peaks are equivalent in height could be found to predict the time constant correctly.

The following non-limiting example describes methods of preparation of test wafers and sensing characteristic images for identifying certain defect states, chemical states, electrostatic states and mechanical features present on a semiconductor wafer surface.

EXAMPLE

Sample wafers can be created by dip coating the wafer 15 in solutions that contain known concentrations of contaminants. Part of this example describes metal contaminants such as Cu and Fe, although any manner of chemical contaminants can be evaluated in this way. The wafer 15 described is either a 100 mm or 150 mm wafer, although these examples apply to any size wafer. The wafer surface 16 is prepared by dipping in HF to remove oxides. The wafer 15 is then cleaned and partially dipped in the metal contaminant solution. The amount of solution remaining on the wafer 15, and the resulting concentration of contaminant on the wafer surface 16, is controlled by selecting dip coating parameters such as the extraction rate.

Partial dipping of the test wafer 15 is preferred to create a transition from clean to contaminated areas. Because the nvCPD signal is differential, the nvCPD sensor 12 detects changes on the wafer surface 16, as opposed to an absolute value relating to surface condition. This aspect of nvCPD sensors 12 is offset by the ability to rapidly image and detect localized contamination anywhere on the surface of the wafer 15.

Figure 7:
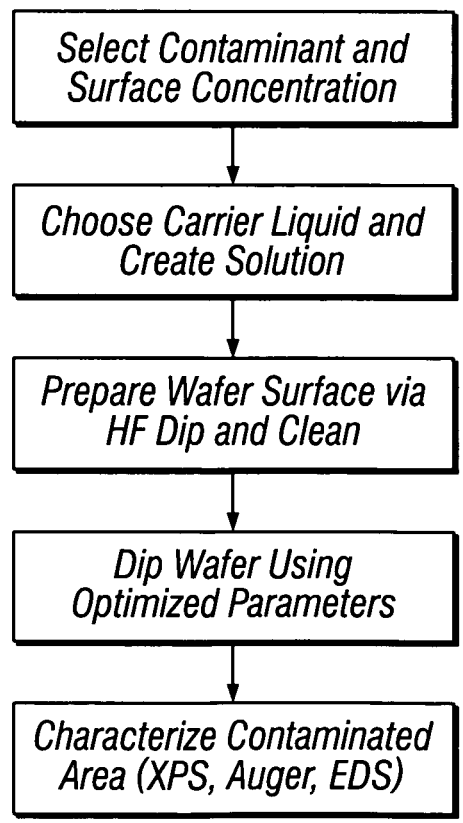
FIG. 7 illustrates steps for creating test wafers which are partially coated with known concentrations of contaminants.

After preparation, each test wafer 15 can be, if necessary, analyzed using an appropriate combination of XPS, Auger, and RBS (or other well known surface analysis methods) techniques to measure actual contaminant concentrations in the dipped areas of the wafer 15. Each step involved in the sample wafer preparation process is shown in FIG. 7. In a production line methodology, standards can be established correlating measure actual contamination concentration to nvCPD data for routine use.

After each sample wafer 15 is created, it can be imaged using a radially scanning nvCPD imaging system 10 constructed in accordance with the invention. As described before, FIGS. 8A and 8B show basic forms of the nvCPD imaging system 10, and FIG. 9 shows another flow diagram illustration of wafer processing. The system 10 employs the nvCPD sensor 12 mounted on the previously described three-axis positioning system 26. This positioning system 26 is used to position the nvCPD sensor 12 above the wafer surface 16 to be imaged, and to scan the nvCPD sensor 12 radially across the wafer surface. The wafer 15 is mounted on a spindle that rotates at high speed (1800 rpm) beneath the nvCPD sensor 12. The system 10 operates by acquiring multiple consecutive tracks of data as the nvCPD sensor 12 is stepped along the radius of rotation of the wafer 15.

Figure 10A:
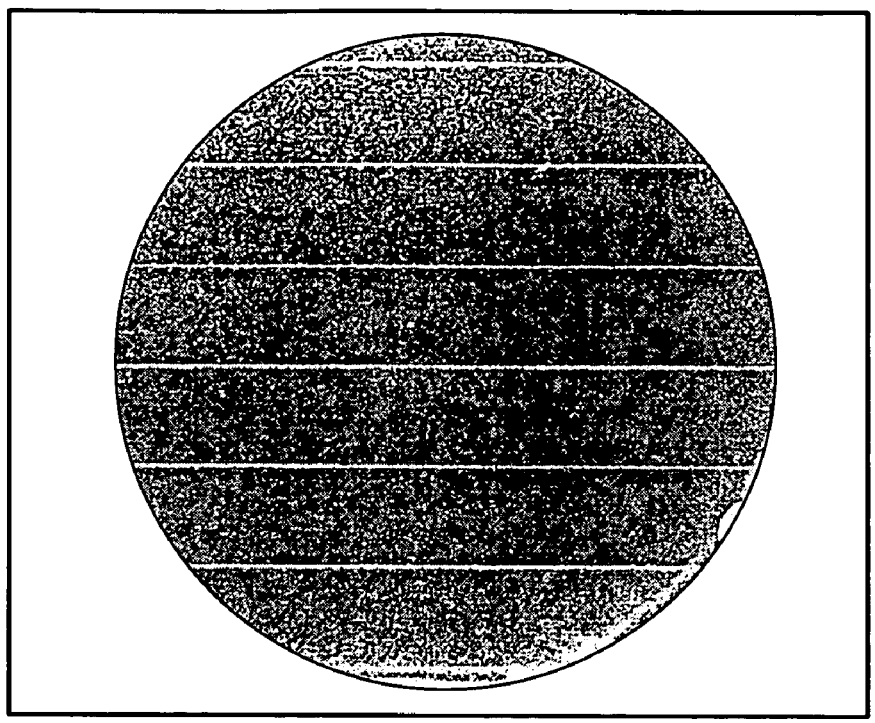
FIG. 10A illustrates an optical image of a 100 mm diameter silicon wafer after application of a vacuum pick-up device and FIG. 10B illustrates an nvCPD image of the wafer of FIG. 10A.
Figure 10B:
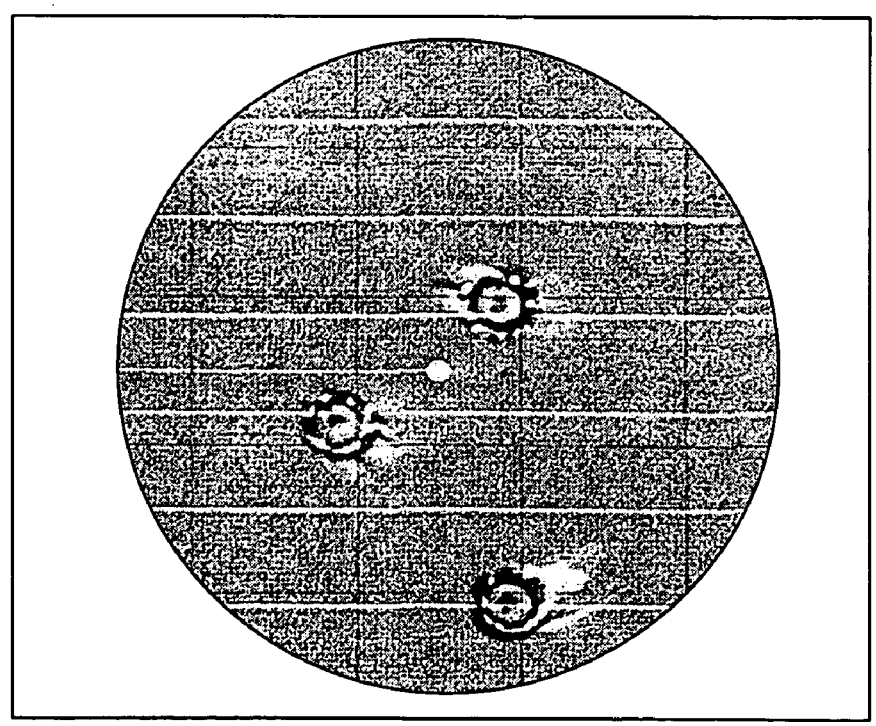

The imaging system 10 has been used for a variety of surface analysis experiments. FIGS. 10A, 10B, 11A, and 11B show sample wafer images that were generated using the nvCPD sensor 12 imaging for wafer inspection. The images show optical images in FIG. 10A and 11A and nvCPD images in FIG. 10B and 11B of a 100 mm form of the wafers 15. The first wafer 15 was cleaned, and then a small vacuum pick-up device was attached to the surface of the wafer 15 in three locations. The optical image of FIG. 10A shows no evidence of any change on the surface 16 of the wafer 15. The nvCPD image of FIG. 10B shows a very large signal at the locations where the pick-up device was applied. The nvCPD signal is believed to be the result of a small amount of residue left on the surface 16 by the pick-up device.

Figure 11A:
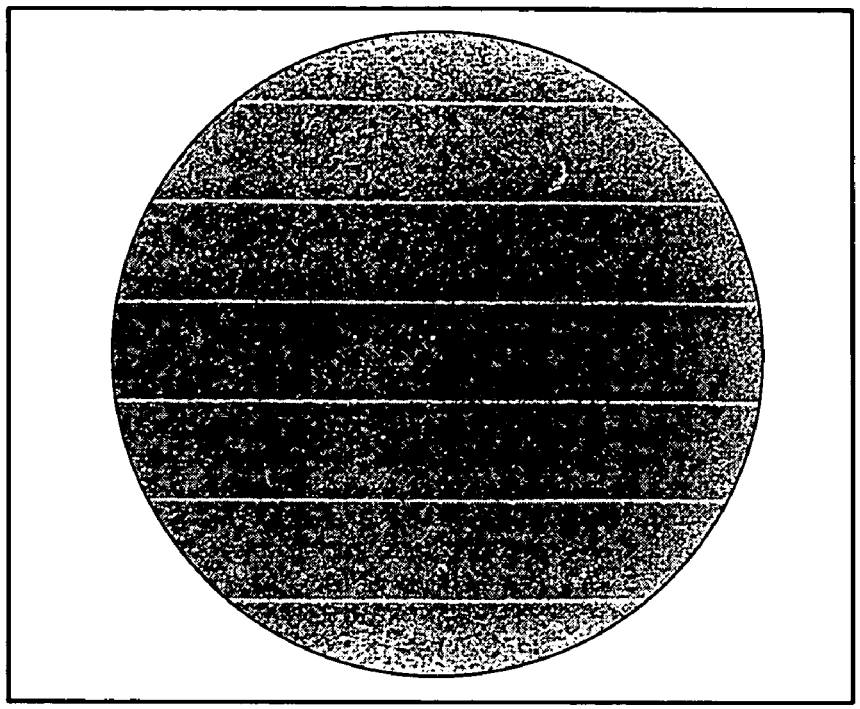
FIG. 11A illustrates an optical image of a second silicon wafer after applying alcohol while spinning the wafer and allowing the alcohol to dry and FIG. 11B is an nvCPD image of the same wafer of FIG. 11A.
Figure 11B:
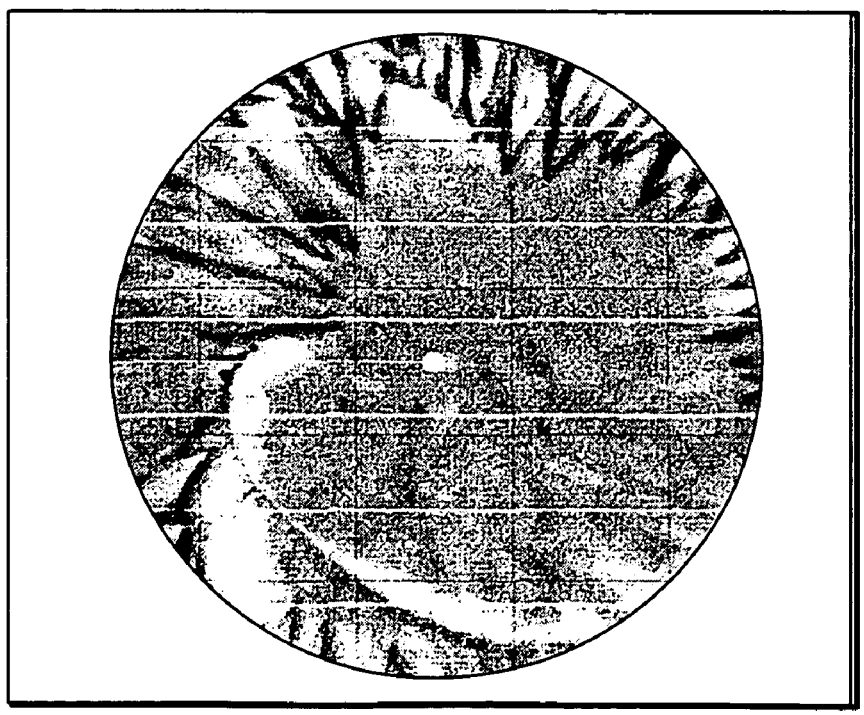

The second set of images in FIGS. 11A and 11B show a wafer 15 that has had alcohol spun-on and then dried. The resulting residue is not visible in the optical image FIG. 11A, but is clearly visible in the nvCPD image FIG. 11B. These images provide a clear demonstration of the usefulness of nvCPD sensor 12 for wafer inspection. Through careful measure of a full mage of defect states and chemical constituents it is possible to correlate an image with a particular chemical state, defect, or combination thereof.

Figure 12A:
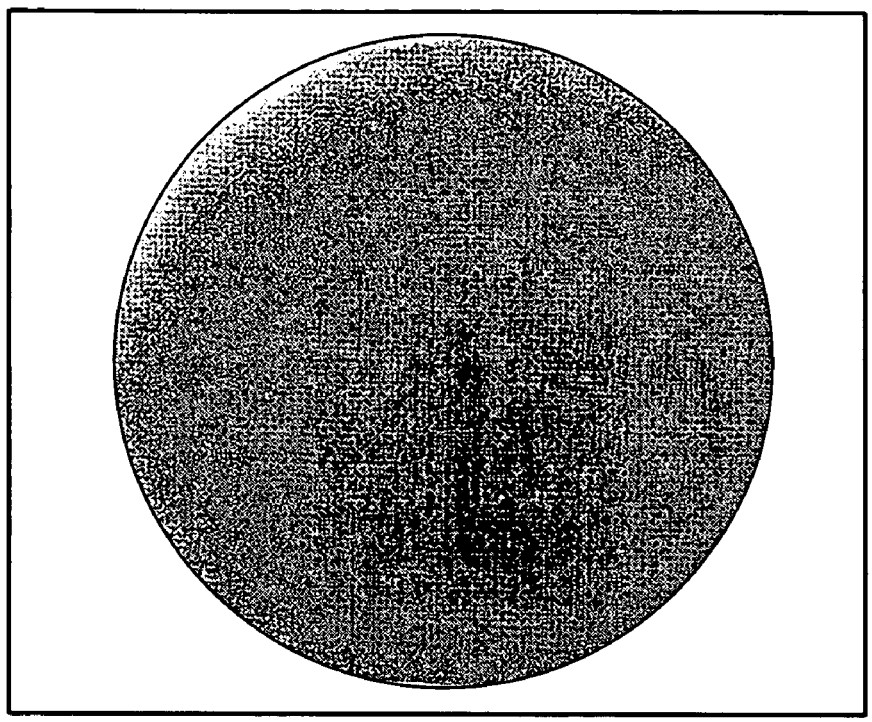
FIG. 12A illustrates an optical image of a silicon wafer after application of a latex glove mark and FIG. 12B is an nvCPD image of the same wafer of FIG. 12A.
Figure 12B:
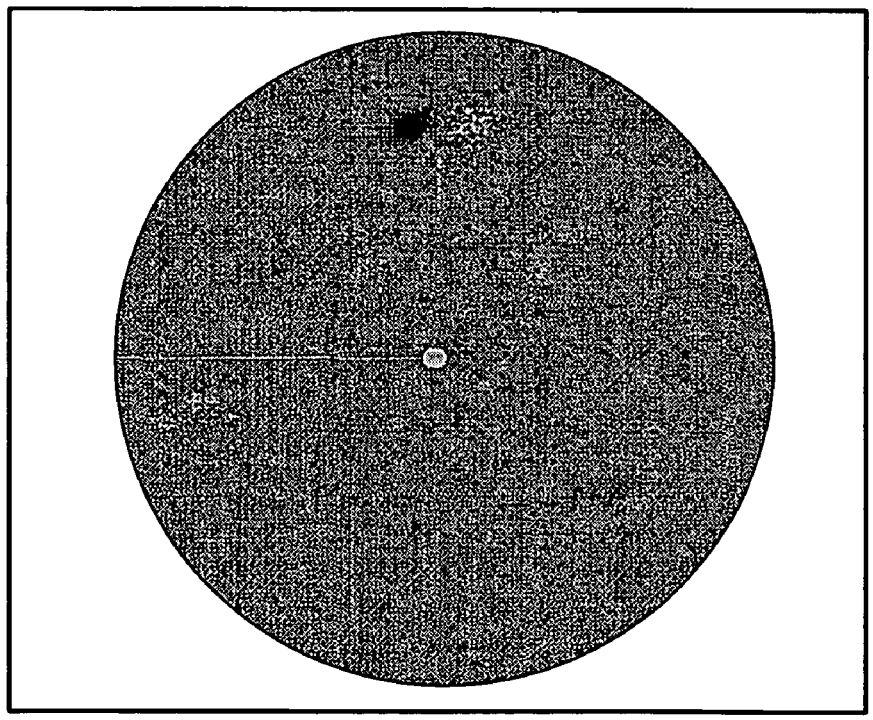
Figure 13A:
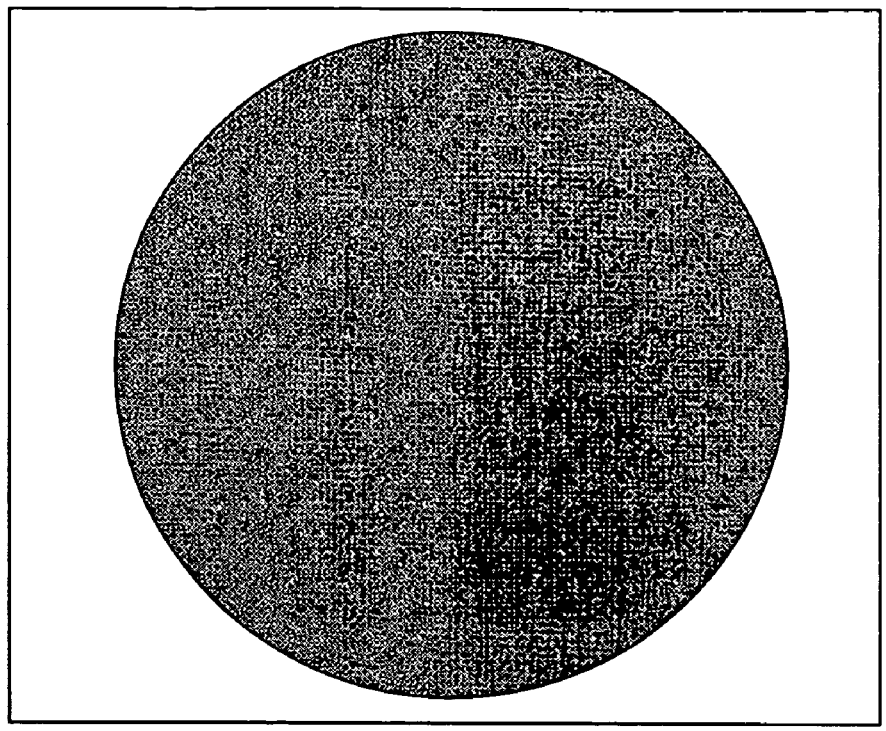
FIG. 13A illustrates an optical image of a silicon wafer having human fingerprints on the wafer and FIG. 13B illustrates an nvCPD image of the wafer of FIG. 13A.
Figure 13B:
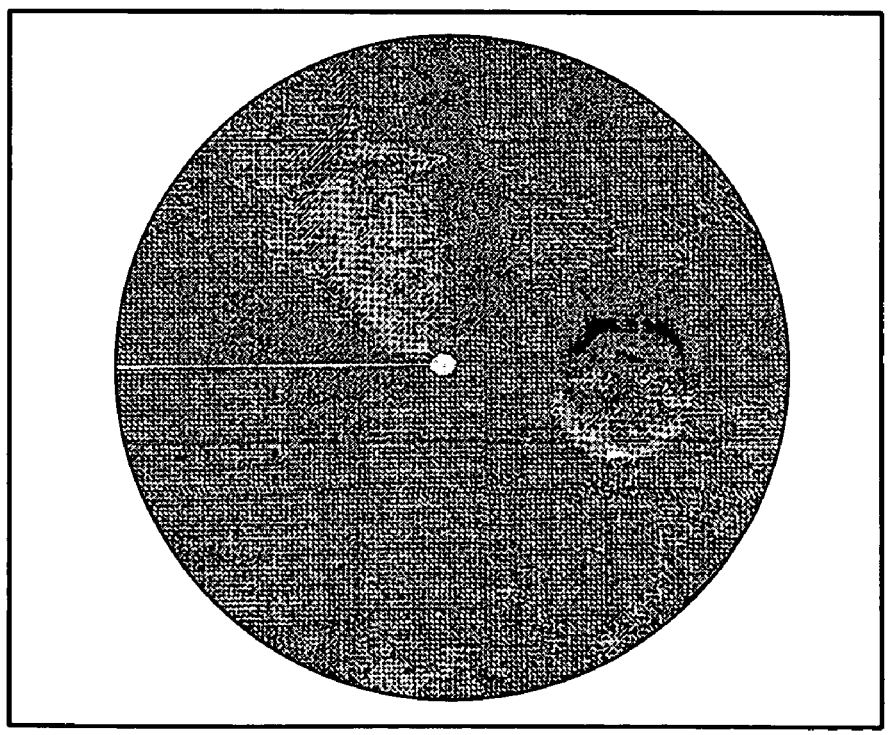
Figure 14:
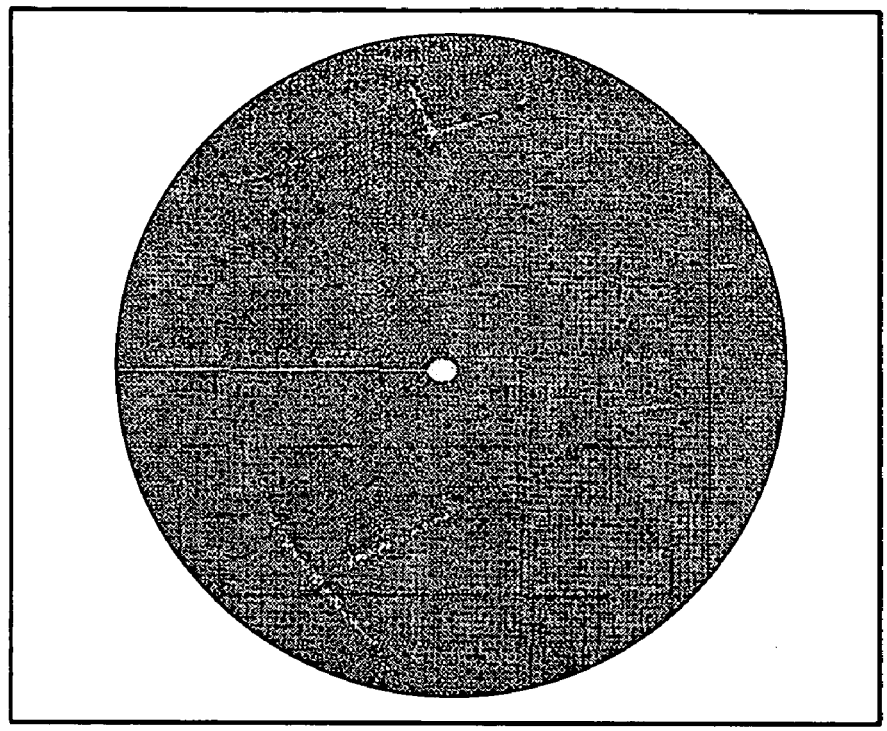
FIG. 14 illustrates an nvCPD image of a silicon wafer after brushing the wafer surface with a stainless steel tool.
Figure 15:
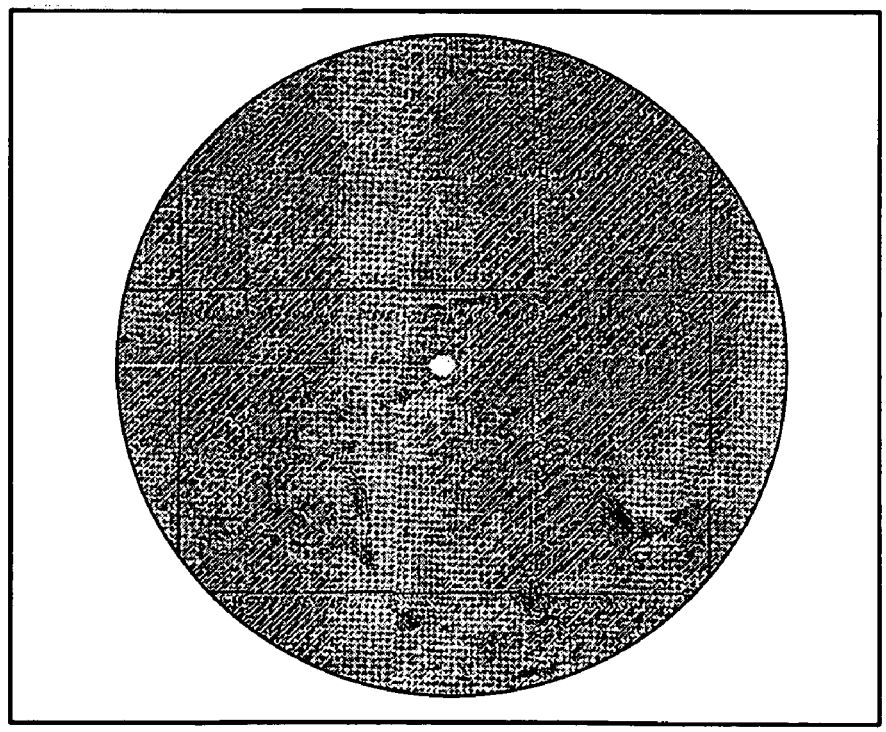
FIG. 15 illustrates an nvCPD image of a silicon wafer after pressing an aluminum fixture onto the wafer surface.

FIGS. 12A and 12B show, respectively, an optical image of latex glove marks and a nvCPD image of latex glove marks. FIGS. 13A and 13B show, respectively, an optical image of human fingerprints and an nvCPD image of the fingerprints. FIG. 14 shows a nvCPD image of a wafer 15 after brushing the wafer 15 with a stainless steel tool, and FIG. 15 shows a nvCPD image of the wafer 15 after pressing an aluminum fixture onto the wafer surface 16. All these example images were acquired using the nvCPD sensor 12 with the probe sensor tip 14 having a diameter of approximately 60 microns measured over a period of approximately 30 seconds.

While preferred embodiments of the invention have been shown and described, it will be clear to those skilled in the art that various changes and modifications can be made without departing from the invention in its broader aspects as set forth in the claims provided hereinafter.

What is claimed is:

1. A method of identifying a defect and performing a quality inspection comprising the steps of:

providing a wafer having a surface;

providing a non-vibrating contact potential difference sensor;

scanning the semiconductor wafer relative to the non-vibrating contact potential difference sensor, the scanning step generating a signal from changes in contact potential difference;

generating contact potential difference data from the signal from changes in contact potential difference;

processing the non-vibrating contact potential difference sensor data to automatically detect a pattern that represents the defect; and outputting the pattern that represents the defect in order to carry out a quality inspection of the wafer.

2. The method as defined in claim 1 further comprising the step of determining a scanning height of the non-vibrating contact potential difference sensor to provide an improved quality inspection of the wafer.

3. The method as defined in claim 2, wherein the step of determining the scanning height comprises positioning a height sensor that is fixed relative to the non-vibrating contact potential difference sensor;

measuring a distance between the height sensor and the wafer; and correlating the height sensor measurements with the non-vibrating contact potential difference sensor position.

4. The method as defined in claim 3, wherein the step of determining the scanning height further comprises providing a time-varying bias voltage, and further wherein the height sensor is the non-vibrating contact potential difference sensor.

5. The method as defined in claim 1, further comprising the step of determining a reference point for optimizing the quality inspection of the wafer.

6. The method as defined in claim 5, wherein the reference point is the center of the wafer as determined by:
   positioning the non-vibrating contact potential difference sensor above the wafer;
   spinning the wafer;
   detecting at least three features on the surface of the wafer; and
   calculating the center of the circle defined by the at least three features.

7. The method as defined in claim 6, further comprising the step of determining a height profile of the wafer by the steps of:
   positioning the height sensor above the center of the spinning wafer; and
   moving the height sensor to the outer edge of the wafer.

8. The method as defined in claim 7, further comprising the step of determining the diameter of the wafer.

9. The method as defined in claim 1, further including the step of reducing noise in the contact potential difference data which comprises deconvoluting the contact potential difference data for improving the quality inspection of the wafer.

10. The method as defined in claim 1 further comprising the step of reducing the noise in the non-vibrating contact potential difference data for improving the quality inspection of the wafer.

11. The method as defined in claim 10, wherein the step of reducing the noise further comprises:
    decomposing the non-vibrating contact potential difference data into a wavelet domain;
    producing a series of wavelet coefficients at a finite number of scales;
    reconstructing the data using only fine scales; and
    shrinking the fine scales based on a given threshold.

12. The method as defined in claim 11, wherein the peak signal is selected by selecting only wavelet coefficients at fine scales and by shrinking the fine scale coefficients based on a threshold.

13. The method as defined in claim 12 wherein the threshold is determined by a wavelet thresholding method selected from the group consisting of "Visu", "SURE", "Hybrid", and "MiniMax".

14. The method as defined in claim 1, further comprising the step of removing a time delay from the non-vibrating contact potential difference sensor data for improving the quality inspection of the wafer.

15. The method as defined in claim 1 further including the steps of:
    displaying the contact potential difference data on a display to generate a characteristic wafer image; and
    comparing the characteristic wafer image with stand images to identify the category of defect present on the surface of the wafer.

16. The method as defined in claim 1, wherein the step of processing the sensor data includes assembling of the data from the contact potential difference sensor into an image that is displayed to the user for evaluation by the user.

17. The method as defined in claim 1, wherein the step of processing the sensor data includes automatically processing the contact potential difference data to identify the category of defect detected.

18. The method as defined in claim 1, wherein the scanning step includes moving the wafer.

19. The method as defined in claim 18, wherein the step of moving the wafer comprises spinning the wafer.

20. The method as defined in claim 1, wherein the wafer includes at least one additional layer disposed on a base silicon wafer.

21. The method as defined in claim 1, wherein the defect is taken from the group consisting of a mechanical defect, a chemical defect, an electronic defect, and combinations thereof.

22. The method as defined in claim 1, wherein the step of scanning comprises the sensor being displaced relative to a fixed form of the wafer.

23. The method as defined in claim 1, wherein the step of scanning includes moving both the wafer and the sensor.

24. The method as defined in claim 1, wherein the step of comparing comprises performing a pattern recognition methodology.

25. The method as defined in claim 1 further comprising the step of processing the wafer with a treatment for ameliorating the category of defect identified.

26. The method as defined in claim 1 further comprising the step of performing a supplementary analysis.

27. The method as defined in claim 26, wherein the step of performing a supplementary analysis comprises analyzing chemical contaminants.

28. The method as defined in claim 27, wherein the step of analyzing chemical contaminants comprises at least one of x-ray photoelectron spectroscopy, Auger spectroscopy and Rutherford backscattering.

29. The method as defined in claim 1 further including the step of applying a computerized decisional methodology to reject selected ones of the semiconductor wafers having an unwanted category of defect.

30. The method as defined in claim 1 further including the step of detecting the defect using an edge detection application.

31. The method as defined in claim 30, wherein detecting the defect using the edge detection application comprises the steps of:
    generating a CPD sensor peak signal at a boundary between two different areas;
    applying an Edge detection application at more than one resolution with different thresholds; and
    quantifying contamination level by the edge area over the total wafer area.

32. A method of denoising signal data from a non-vibrating contact potential difference sensor inspecting a wafer, comprising the steps of:
    generating signal data from a contact potential difference sensor characteristic of a surface of a wafer;
    decomposing the signal data into a wavelet domain;
    obtaining a plurality of coefficients at a finite number of scales;
    selecting for a peak signal selected by selecting only wavelet coefficients at fine scales and by shrinking the fine scale coefficients based on a threshold;
    reconstructing the data by the coefficients in reverse order; and
    outputting the reconstructed data to carry out an improved quality inspection of the wafer.

33. The method of claim 32, wherein the threshold is determined by a wavelet thresholding method selected from the group consisting of "Visu", "SURE", "Hybrid", and "MiniMax".

34. The method of claim 32, wherein the signal data is decomposed into the wavelet domain using a wavelet selected from the group consisting of "Coiflet", "Daubechies", and "Symmlet".

35. A method of removing a time delay from a non-vibrating contact potential difference sensor signal from inspecting a wafer, comprising the steps of:
generating a non-vibrating contact potential difference sensor signal characteristic of a wafer;
modeling a circuit as a first order RC circuit;
converting the non-vibrating contact potential difference sensor signal into a discrete time transfer function;
determining the impulse response of the discretized time transfer function;
deconvoluting each data track separately to produce a deconvoluted sensor signal; and
outputting the deconvoluted sensor signal to carry out a quality inspection of the wafer.

36. A system for identifying a category of defect on a surface of a wafer, comprising:
a non-vibrating contact potential difference sensor;
a height sensor for measuring height of the contact potential difference sensor above the surface of the wafer to control the height and thereby produce repeatable identification of the category of defect;
a device for moving the non-vibrating contact potential difference sensor relative to the semiconductor wafer; and
a computer for receiving and analyzing wafer data generated by the non-vibrating contact potential difference sensor and the height sensor and processing the non-vibrating contact potential difference sensor and the height sensor data to automatically detect a pattern that represents a defects.

37. The system as defined in claim 36, wherein the height sensor is a non-vibrating contact potential difference sensor.

38. The system as defined in claim 36 further including a data base of images of standard defects, and wherein the computer including computer software which can analyze the wafer data and compare with the images of standard defects to generate identification information about the type of defect present on the surface of the wafer.

39. The system as defined in claim 36 further including a transport device to move selected ones of the semiconductor wafers to a secondary processing system having a category of defect which can be remedied.

40. The system as defined in claim 39, wherein the transport device comprises a wafer handler.

41. The system as defined in claim 36 further including a plurality of the sensors with one of the sensors disposed immediately downstream from each of a plurality of cleaning systems, thereby enabling monitoring of the semiconductor wafer after processed at each of the cleaning systems.

42. The system as defined in claim 36, further including a mechanism for automatically determining the cleanliness of wafers and modifying cleaning parameters to improve the cleaning process.

43. The system as defined in claim 36, wherein the wafer is a semiconductor wafer.

44. A method of identifying a defect comprising the steps of:
providing a wafer having a surface;
providing a reference source for data processing;
providing a non-vibrating contact potential difference sensor;
scanning the semiconductor wafer relative to the non-vibrating contact potential difference sensor;
generating contact potential difference data from the non-vibrating contact potential difference sensor;
processing the non-vibrating contact potential difference sensor data to automatically detect a pattern that represents the defect with the reference source enabling at least one of signal generation, image production and absolute distance measurement; and
utilizing the pattern that represents the defect to carry out a quality inspection of the wafer.

* * * * *